(12) United States Patent
Jan et al.

(10) Patent No.: US 7,091,390 B2
(45) Date of Patent: Aug. 15, 2006

(54) HYDROCARBON CONVERSION PROCESSES USING CATALYSTS COMPRISING UZM-8 AND UZM-8HS COMPOSITIONS

(75) Inventors: Deng-Yang Jan, Elk Grove Village, IL (US); Raelynn M. Miller, LaGrange, IL (US); Mathias P. Koljack, Schaumburg, IL (US); John E. Bauer, LaGrange Park, IL (US); Paula L. Bogdan, Mount Prospect, IL (US); Gregory J. Lewis, Santa Cruz, CA (US); Gregory J. Gajda, Mount Prospect, IL (US); Susan C. Koster, Carpentersville, IL (US); Michael G. Gatter, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 128 days.

(21) Appl. No.: 10/828,989

(22) Filed: Apr. 21, 2004

(65) Prior Publication Data

US 2004/0199036 A1    Oct. 7, 2004

Related U.S. Application Data

(63) Continuation-in-part of application No. 10/395,466, filed on Mar. 21, 2003, now Pat. No. 6,756,030, and a continuation-in-part of application No. 10/395,624, filed on Mar. 21, 2003, now abandoned.

(51) Int. Cl.
*C07C 2/68* (2006.01)
*C07C 5/29* (2006.01)
*C07C 2/58* (2006.01)

(52) U.S. Cl. ............... 585/467; 585/481; 585/475; 585/722

(58) Field of Classification Search ............ 585/467, 585/475, 481, 722
See application file for complete search history.

(56) References Cited

U.S. PATENT DOCUMENTS

| 4,610,856 A | 9/1986 | Skeels et al. ............ 423/328 |
| 5,236,575 A | 8/1993 | Bennett et al. ........... 208/46 |
| 5,362,697 A | 11/1994 | Fung et al. .............. 502/71 |

OTHER PUBLICATIONS

D. W. Breck, *Zeolite Molecular Sieves*, Wiley and Sons, New York, (1974), p. 441.
J. Phys. Chem., 1996, 100, pp. 3788-3798.

*Primary Examiner*—Thuan D Dang
(74) *Attorney, Agent, or Firm*—John G. Tolomei; Frank S. Molinaro

(57) ABSTRACT

Hydrocarbon conversion processes using a new family of zeolites identified as UZM-8 and UZM-8HS are described. The UZM-8 and UZM-8HS are related in that the UZM-8HS are derived from the UZM-8 zeolite by treating the UZM-8 with a fluoro-silicate salt, an acid, etc. The UZM-8 and -8HS have unique x-ray diffraction patterns. These zeolites can be used in alkylation of aromatics, transalkylation of aromatics, isomerization of aromatics and alkylation of isoparaffins.

17 Claims, 12 Drawing Sheets

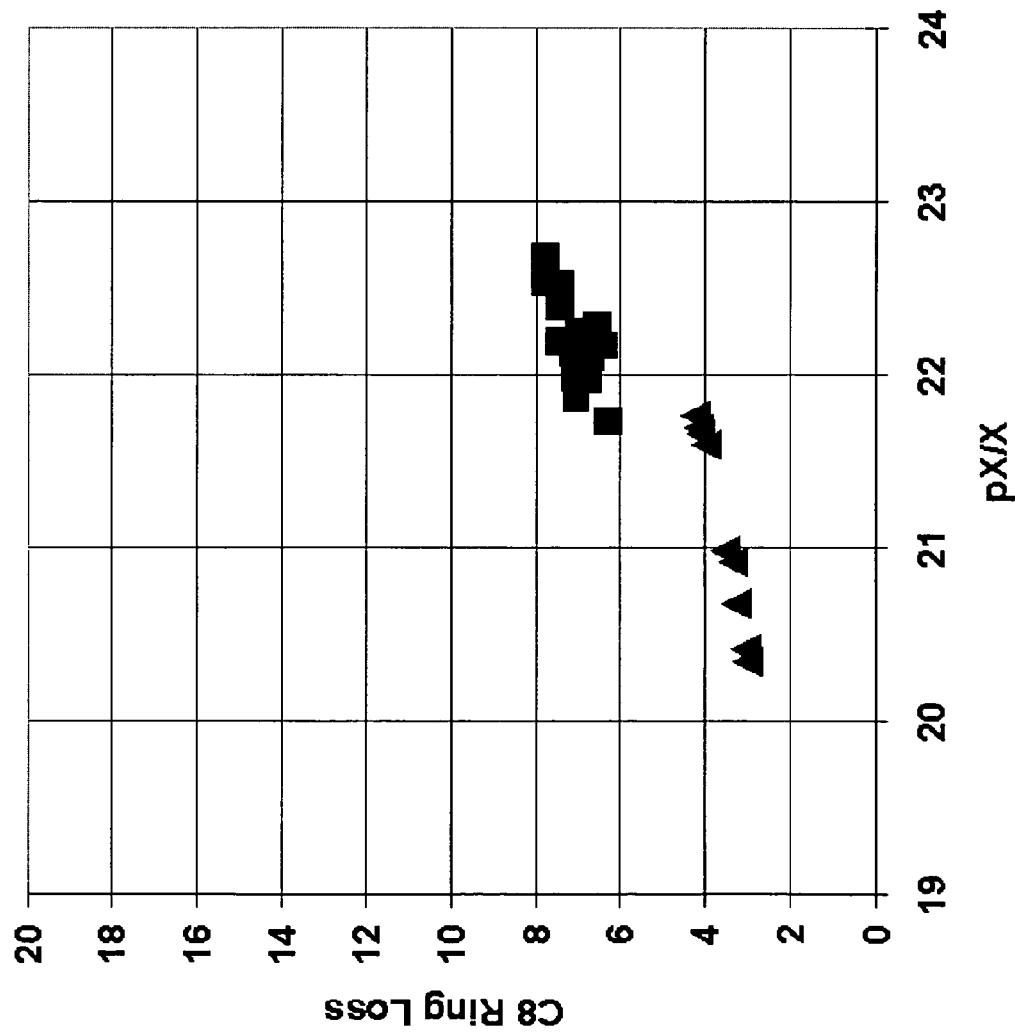

HYDROCARBON CONVERSION PROCESSES USING CATALYSTS COMPRISING UZM-8 AND UZM-8HS COMPOSITIONS

CROSS-REFERENCE TO RELATED APPLICATION

This application is a Continuation-In-Part of copending application Ser. No. 10/395,466 now U.S. Pat. No. 6,756,030 and Ser. No. 10/395,624 both filed Mar. 21, 2003 now abandoned, the contents of which are hereby incorporated by reference in their entirety.

FIELD OF THE INVENTION

This invention relates to hydrocarbon conversion processes using aluminosilicate zeolites designated UZM-8 and UZM-8HS. The hydrocarbon conversion processes are selected from transalkylation of aromatics, alkylation of aromatics, isomerization of aromatics and alkylation of isoparaffins.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al, as well as structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversions, which can take place on outside surfaces as well as on internal surfaces within the pore.

Applicants have synthesized a new family of materials designated UZM-8. The UZM-8 compositions are aluminosilicates having Si/Al molar ratio from about 6.5 to about 35. The UZM-8 compositions show unique x-ray diffraction patterns compared to other known zeolites. These UZM-8 compositions are prepared from aqueous reaction mixtures containing either organoammonium compounds or a mixture of organoammonium compounds and alkali and/or alkaline earth compounds. The organoammonium compounds used to make UZM-8 are non-cyclic nor contain cyclic substituents and are generally quite simple. Preferred examples of organoammonium compounds used to make UZM-8 include the diethyldimethylammonium (DEDMA), ethyltrimethylammonium (ETMA) or hexamethonium (HM) cations.

Although UZM-8 compositions have some similarities to a layered material identified as MCM-56, there are sufficient differences that UZM-8 compositions are structurally different from MCM-56 materials and thus are unique new zeolites structures. The preparation of MCM-56 is disclosed in U.S. Pat. No. 5,362,697 where it is stated that MCM-56 is prepared from a reaction mixture containing a combination of alkali metals and hexamethylene imine (HMI) as directing agents and requires that the silica source be a predominately solid silica source comprising at least 30 wt. % $SiO_2$. It is further stated in the '697 patent that the reaction must be stopped and quenched at a time before significant amounts of MCM-49 form in the reaction mixture. The synthesis of MCM-49 is disclosed in U.S. Pat. No. 5,236,575 and again involves a combination of alkali metals and HMI structure directing agents plus a predominately solid silica source comprising at least 30 wt. % $SiO_2$. Upon calcination the MCM-49 composition is not readily distinguishable from calcined MCM-22 which has the MWW framework topology. It is further stated in J. Phys. Chem., 1996, 100, p.3788–3798, that in the as-synthesized form MCM-49 has essentially the MWW topology. Thus, MCM-56 is an intermediate structure in the formation of MCM-49 which in the calcined form is virtually the same as MCM-22 both of which have the MWW structure. The '697 patent further describes the MCM-56 as a layered structure in both its as-synthesized and calcined forms based on the claimed swellability of the material.

In contrast to MCM-56, UZM-8 is not an intermediate in the formation of MCM-49. Additionally, the UZM-8 materials can be synthesized from an alkali free reaction mixture using an organoammonium cation such as DEDMA cation that offers great stability and robustness without the formation of MCM-49 or other impurities. However, in the HMI/Na system, varying the relative amount of amine structure directing agent to alkali metal and/or alkaline earth metal compound can yield either the MCM-56/MCM-49 system with higher relative alkali content or a precursor to MCM-22 with lower relative alkali content. Reaction conditions, mainly temperature and time, are used to distinguish MCM-56 and MCM-49 in the higher alkali content system that is difficult to control, leading to the requirement for quenching the MCM-56 reaction mixture before significant amounts of MCM-49 form. Finally, UZM-8 is a layered material in that the as-synthesized form is swellable and has a x-ray diffraction pattern that is distinguishable from MCM-56.

The UZM-8 compositions have also been modified by using one or more techniques selected from acid extraction, calcination, steaming and ammonium hexafluorosilicate treatment, applicants have been able to control the aluminum content of the UZM-8 zeolites to nearly all silica while maintaining their structure and porosity. Dealumination strategies are known in the art and are given by Breck (see D. W. Breck, Zeolite Molecular Sieves, Wiley and Sons, New York, (1974), p. 441) and Skeels and Breck (see U.S. Pat. No. 4,610,856). The result is a modified UZM-8 (UZM-8HS) material containing less aluminum than the starting UZM-8 composition. Control of the Al content in the zeolite allows one to tune the properties associated with the Al, such as ion-exchange capacity and acidity thereby providing improved catalysts and/or adsorbents. These modified compositions have been designated UZM-8HS.

SUMMARY OF THE INVENTION

As stated, this invention relates to hydrocarbon processes using UZM-8 and UZM-8HS crystalline aluminosilicate compositions. Accordingly, one embodiment of the invention is a hydrocarbon conversion process comprising contacting a hydrocarbon stream with a catalytic composite at hydrocarbon conversion conditions to give a converted product, the hydrocarbon conversion processes selected from the group consisting of alkylation of aromatics, transalkylation of aromatics, isomerization of aromatics and alkylation of isoparaffins and the catalytic composite selected from the group consisting of UZM-8, UZM-8HS and mixtures thereof.

This and other objects and embodiments will become more apparent after a detailed description of the invention.

Additional objects, embodiments and details of this invention can be obtained from the following detailed description of the invention.

BRIEF DESCRIPTION OF THE DRAWINGS

FIG. 2 presents plots of PX/X (ratio of para-xylene to xylene) versus $C_8$ ring loss for UZM-8 from example 36 and a mordenite reference catalyst.

DETAILED DESCRIPTION OF THE INVENTION

Figure 1A:
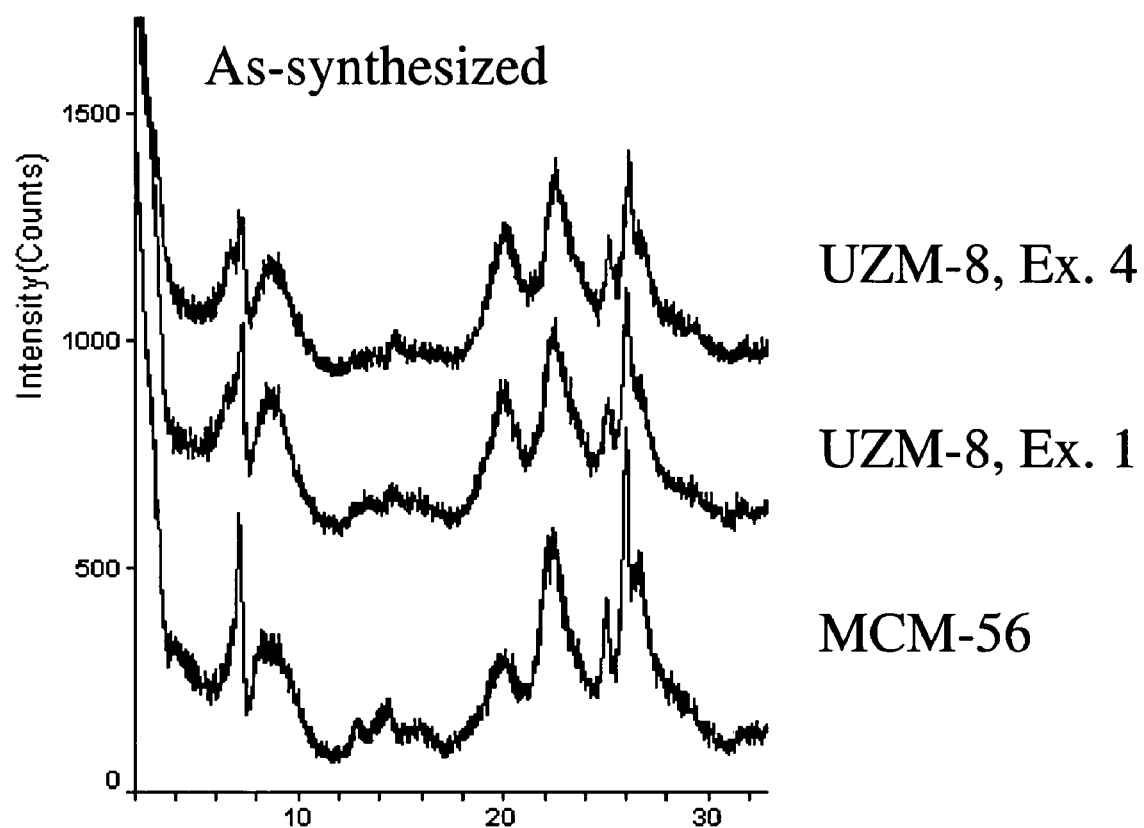
FIG. 1a presents x-ray diffraction patterns for as-synthesized UZM-8 compositions of examples 1 and 4, and for zeolite MCM-56.

The catalytic compositions which are used in the processes of the current invention comprise UZM-8, UZM-8HS and mixtures thereof. UZM-8 zeolites can be prepared in an alkali-free reaction medium in which only one or more organoammonium species are used as structure directing agents. In this case, the microporous crystalline zeolite (UZM-8) has a composition in the as-synthesized form and on an anhydrous basis expressed by the empirical formula:

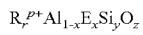

where R is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that that do not contain a cyclic group as one substituent. Of these those that contain at least two methyl groups as substituents are especially preferred. Examples of preferred cations include without limitation DEDMA, ETMA, HM and mixtures thereof. The ratio of R to (Al+E) is represented by "r" which varies from about 0.05 to about 5. The value of "p" which is the weighted average valence of R varies from 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation:

$$z = (r \cdot p + 3 + 4 \cdot y)/2$$

The UZM-8 zeolites can also be prepared using both organoammonium cations and alkali and/or alkaline earth cations as structure directing agents. As in the alkali-free case above, the same organoammonium cations can be used here. Alkali or alkaline earth cations are observed to speed up the crystallization of UZM-8, often when present in amounts less than 0.05 $M^+/Si$. For the alkali and/or alkaline earth metal containing systems, the microporous crystalline zeolite (UZM-8) has a composition in the as-synthesized form and on an anhydrous basis expressed by the empirical formula:

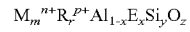

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. Preferred R cations include without limitation DEDMA, ETMA, HM and mixtures thereof. The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation:

$$z = (m \cdot n + r \cdot p + 3 + 4 \cdot y)/2$$

where M is only one metal, then the weighted average valence is the valence of that one metal, i.e. +1 or +2. However, when more than one M metal is present, the total amount of

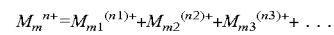

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

Similarly when only one R organic cation is present, the weighted average valence is the valence of the single R cation, i.e., +1 or +2. When more than one R cation is present, the total amount of R is given by the equation:

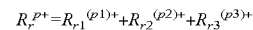

and the weighted average valence "p" is given by the equation:

$$p = \frac{p_1 \cdot r_1 + p_2 \cdot r_2 + p_3 \cdot r_3 + \ldots}{r_1 + r_2 + r_3 + \ldots}$$

The microporous crystalline zeolites of the present invention are prepared by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited the hydroxide, chloride, bromide, iodide and fluoride compounds. Specific examples include without limitation DEDMA hydroxide, ETMA hydroxide, tetramethylammonium hydroxide, tetraethylammonium hydroxide, hexamethonium bromide, tetrapropylammonium hydroxide, methyltriethylammonium hydroxide, tetramethylammonium chloride and choline chloride. R may also be introduced as an amine, diamine, or alkanolamine that subsequently hydrolyzes to form an organoammonium cation. Specific non-limiting examples are N,N,N',N'-tetramethyl-1,6-hexanediamine, triethylamine, and triethanolamine. Preferred sources of R without limitation are ETMAOH, DEDMAOH, and HM(OH)$_2$.

The reaction mixture containing reactive sources of the desired components can be described in terms of molar ratios of the oxides by the formula:

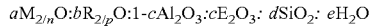

$aM_{2/n}O:bR_{2/p}O:1-cAl_2O_3:cE_2O_3: dSiO_2: eH_2O$ where "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products. The reaction mixture is now reacted at a temperature of about 85° C. to about 225° C. and preferably from about 125° C. to about 150° C. for a period of about 1 day to about 28 days and preferably for a time of about 5 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The UZM-8 aluminosilicate zeolite, which is obtained from the above-described process, is characterized by an x-ray diffraction pattern, having at least the d-spacings and relative intensities set forth in Table A.

TABLE A d-Spacings and Relative Intensities for as-synthesized UZM-8

| 2-θ | d(Å) | I/I$_0$% |
|---|---|---|
| 6.40–6.90 | 13.80–12.80 | w–s |
| 6.95–7.42 | 12.70–11.90 | m–s |
| 8.33–9.11 | 10.60–9.70 | w–vs |
| 19.62–20.49 | 4.52–4.33 | m–vs |
| 21.93–22.84 | 4.05–3.89 | m–vs |
| 24.71–25.35 | 3.60–3.51 | w–m |
| 25.73–26.35 | 3.46–3.38 | m–vs |

The UZM-8 compositions are stable to at least 600° C. and usually at least 700° C. The characteristic diffraction lines associated with typical calcined UZM-8 samples are shown below in Table B. The as-synthesized form of UZM-8 is expandable with organic cations, indicating a layered structure.

TABLE B d-Spacings and Relative Intensity for Calcined UZM-8

| 2-θ | d(Å) | I/I$_0$% |
|---|---|---|
| 4.05–4.60 | 21.80–19.19 | w–m |
| 7.00–7.55 | 12.62–11.70 | m–vs |
| 8.55–9.15 | 10.33–9.66 | w–vs |
| 12.55–13.15 | 7.05–6.73 | w |
| 14.30–14.90 | 6.19–5.94 | m–vs |
| 19.55–20.35 | 4.54–4.36 | w–m |
| 22.35–23.10 | 3.97–3.85 | m–vs |
| 24.95–25.85 | 3.57–3.44 | w–m |
| 25.95–26.75 | 3.43–3.33 | m–s |

An aspect of the UZM-8 synthesis that contributes to some of its unique properties is that it can be synthesized from a homogenous solution. In this chemistry, soluble aluminosilicate precursors condense during digestion to form extremely small crystallites that have a great deal of external surface area and short diffusion paths within the pores of the crystallites. This can affect both adsorption and catalytic properties of the material.

As-synthesized, the UZM-8 material will contain some of the charge balancing cations in its pores. In the case of syntheses from alkali or alkaline earth metal-containing reaction mixtures, some of these cations may be exchangeable cations that can be exchanged for other cations. In the case of organoammonium cations, they can be removed by heating under controlled conditions. In the cases where UZM-8 is prepared in an alkali-free system, the organoammonium cations are best removed by controlled calcination, thus generating the acid form of the zeolite without any intervening ion-exchange steps. On the other hand, it may sometimes be possible to remove a portion of the organoammonium via ion exchange. In a special case of ion exchange, the ammonium form of UZM-8 may be generated via calcination of the organoammonium form of UZM-8 in an ammonia atmosphere.

The properties of the UZM-8 compositions described above can be modified by removing some of the aluminum atoms from the framework and optionally inserting silicon atoms. Treating processes include without limitation treatment with a fluorosilicate solution or slurry, extraction with a weak, strong or complexing acid, etc. In carrying out these dealumination treatments, the particular form of the UZM-8 is not critical, but can have a bearing on the final product especially with regard to the extent of dealumination.

Thus, the UZM-8 can be used as synthesized or can be ion exchanged to provide a different cation form. In this respect, the starting zeolite can be described by the empirical formula:

$$M'^{n'+}_{m'} R^{p+}_{r'} Al_{(1-x)} E_x Si_y O_{z'}$$

where R, x, y, and E are as described above and m' has a value from 0 to about 7.0, M' is a cation selected from the group consisting of alkali metals, alkaline earth metals, rare earth metals, hydrogen ion, ammonium ion, and mixtures thereof, n' is the weighted average valence of M' and varies from about 1 to about 3, r' has a value from 0 to about 7.0, r'+m'>0, and p is the weighted average valence of R and varies from about +1 to +2. The value of z' is given by the formula:

$$z' = (m' \cdot n' + r' \cdot p + 3 + 4 \cdot y)/2$$

The designation UZM-8 will be used to refer to the zeolite represented by formula (2) which includes both the as-synthesized and ion exchanged forms of the zeolite. The modified compositions will be referred to as UZM-8HS.

Methods used to exchange one cation for another are well known in the art and involve contacting the microporous compositions with a solution containing the desired cation (at molar excess) at exchange conditions. Exchange conditions include a temperature of about 15° C. to about 100° C. and a time of about 20 minutes to about 50 hours. The organic cation can also be removed prior to ion exchange by heating under controlled conditions. A special case of ion-exchange is ammonia calcination, in which the organic template can be decomposed and replaced by ammonium cation.

In a preferred case, especially for dealumination by treatment with a fluorosilicate solution, the UZM-8 is exchanged with ammonium cation by contacting it with ammonium nitrate at a temperature of 15° C. to about 100° C., followed by a water wash. This procedure may be repeated several times. Finally, the exchanged UZM-8 zeolite is dried at 100° C.

One process of preparing the UZM-8HS compositions is by treating the UZM-8 composition described above with a fluorosilicate salt at a temperature of about 20° C. to about 90° C. The fluorosilicate salt serves two purposes. It removes aluminum atoms from the framework and provides a source of extraneous silicon, which can be inserted into the framework (replacing the aluminum). The fluorosilicate salts which can be used are described by the general formula:

$$A_{2/n} SiF_6$$

where n is the valence of A and A is a cation selected from the group consisting of $NH_4^+$, $H^+$, $Mg^{2+}$, $Li^+$, $Na^+$, $Ba^{2+}$, $Cd^{2+}$, $Cu^+$, $Ca^{2+}$, $Cs^+$, $Fe^{2+}$, $Ca^{2+}$, $Pb^{2+}$, $Mn^{2+}$, $Rb^+$, $Ag^+$, $Sr^{2+}$, $Tl^+$, and $Zn^{2+}$. The ammonium fluorosilicate is most preferred because of its substantial solubility in water and because it forms water soluble by-product salts upon reaction with the zeolite, namely $(NH_4)_3 AlF_6$.

The fluorosilicate salt is contacted with the UZM-8 zeolite in the form of an aqueous solution or slurry at a pH in the range of about 3 to about 7. This solution is contacted with the zeolite either incrementally or continuously at a slow rate such that a sufficient proportion of the framework aluminum atoms removed are replaced by silicon atoms to retain at least 50%, preferably at least 70% of the framework (crystalline) structure of the starting UZM-8 zeolite. The amount of fluorosilicate necessary to carry out the process of this invention can vary considerably, but should be at least in an amount of 0.0075 moles of the fluorosilicate salt per 100 grams of starting zeolite. Once the reaction is complete, the product zeolite UZM-8HS is isolated by conventional techniques such as filtration.

Without wishing to be bound by any particular theory, the process of removing aluminum and inserting the silicon appears to proceed in two steps in which the aluminum extraction step will, unless controlled, proceed very rapidly while the silicon insertion is relatively slow. If dealumination becomes too extensive without silicon substitution, the crystal structure becomes seriously degraded and ultimately collapses. In general, the rate of aluminum extraction is decreased as the pH of the fluorosilicate solution in contact with the zeolite is increased within the range of about 3 to about 7 and as the concentration of the fluorosilicate in the reaction system is decreased. At pH values below 3, crystal degradation can be unduly severe, whereas at pH values higher than 7, silicon insertion is unduly slow. Also, increasing the reaction temperature tends to increase the rate of substitution of silicon. Increasing the reaction temperature has been found to have less of an effect on dealumination than the pH of the solution. Therefore, the pH may be considered a means of controlling the dealumination while temperature may be considered as a means of controlling the substitution rate.

Theoretically, there is no lower limit for the concentration of fluorosilicate salt in the aqueous solution employed, provided, of course, the pH of the solution is high enough to avoid undue destructive attack on the UZM-8 zeolite structure apart from the intended reaction with the fluorosilicate. A slow rate of addition of fluorosilicate salts insures that adequate time is permitted for the insertion of silicon into the framework before excessive aluminum extraction occurs with consequent collapse of the crystal structure. In general the effective reaction temperature is between about 10° C. and 99° C., preferably between about 20° C. and 95° C., but temperatures of 125° C. or higher and as low as 0° C. can be used.

The maximum concentration of fluorosilicate salt in the aqueous solution employed is, of course, interrelated to the temperature and pH factors and also with the time of contact between the zeolite and the solution and the relative proportions of zeolite and fluorosilicate salt. Solutions having fluorosilicate salt concentrations of between $10^{-3}$ moles per liter of solution and up to saturation of the solution can be employed, but it is preferred that concentrations in the range of between about 0.05 and about 2.0 moles per liter of solution be used. In addition, as hereinbefore discussed, slurries of the fluorosilicate salts may be employed. The aforementioned concentration values are with respect to true solutions, and are not intended to apply to the total fluorosilicate salts in slurries of the salts in water. Even very slightly soluble fluorosilicate salts can be slurried in water and used as a reagent, the undissolved solids being readily available to replace dissolved molecular species consumed in reaction with the zeolite. The minimum value for the amount of fluoro salt to be added is preferably at least equivalent to the minimum mole fraction of aluminum to be removed from the zeolite.

It has been found that when large amounts of silicon atoms are to be substituted, i.e., increasing the $SiO_2/Al_2O_3$ ratio by more than 100%, it is preferable to carry out the process in multiple steps in order to minimize crystal degradation. As the amount of silicon that is substituted into the framework is substantially increased (beyond 100% increase) it may actually be necessary to carry out the process in two or more steps in order to prevent excessive degradation of the crystalline structure. That is, contacting with the fluorosilicate salt is carried out in two or more steps using a lower concentration of the fluorosilicate salt than required to replace the desired amount of silicon in one step. After each fluorosilicate treatment, the product is washed to remove fluoride and aluminum. Drying of the zeolite at 50° C. between treatments may also be done to facilitate the handling of the wet zeolite product.

Another treatment method involves contacting the UZM-8 starting zeolite with an acid (acid extraction) in order to remove some of the aluminum from the framework and thereby provide the UZM-8HS zeolite. Although it is known that aluminum can be extracted from the framework by acids, it is not predictable whether the resulting product will retain a substantial portion of its crystallinity or whether the structure will collapse resulting in an amorphous material. Applicants have discovered that UZM-8 can be dealuminated to nearly pure silica forms while maintaining substantial crystallinity, surface area and micropore volume.

The acids which can be used in carrying out acid extraction include without limitation mineral acids, carboxylic acids and mixtures thereof. Examples of these include sulfuric acid, nitric acid, ethylene diaminetetraacetic acid (EDTA), citric acid, oxalic acid, etc. The concentration of acid which can be used is not critical but is conveniently between about 1 wt. % to about 80 wt. % acid and preferably between 5 wt. % and 40 wt. % acid. Acid extraction conditions include a temperature of about 10° C. to about 100° C. for a time of about 10 minutes to about 24 hours. Once treated with the acid, the UZM-8HS zeolite is isolated by means such as filtration, washed with deionized water and dried at ambient temperature up to about 100° C.

The extent of dealumination obtained from acid extraction depends on the cation form of the starting UZM-8 as well as the acid concentration and the time and temperature over which the extraction is conducted. For example, if organic cations are present in the starting UZM-8, the extent of dealumination will be slight compared to a UZM-8 in which the organic cations have been removed. This may be preferred if it is desired to have dealumination just at the surface of the UZM-8. Convenient ways of removing the organic cations include calcination, ammonia calcination, steaming and ion exchange. Calcination conditions include a temperature of about 300° C. to about 600° C. for a time of about 2 to about 24 hours. Steaming conditions include a temperature of about 400° C. to about 850° C. with from about 1% to about 100% steam for a time of about 10 minutes to about 48 hours and preferably a temperature of about 500° C. to about 600° C., steam concentration of about 5 to about 50% and a time of about 1 to about 2 hours. Ion exchange conditions are as set forth above.

A special treatment for removing organic cations to obtain the ammonium ion exchanged form is ammonia calcination. Calcination in an ammonia atmosphere can decompose organic cations, presumably to a proton form that can be neutralized by ammonia to form the ammonium cation. The stability of the ammonium form of the zeolite prevents dealumination upon hydration, which occurs extensively in lower ratio zeolites in the proton forms obtained in air calcinations. The resulting ammonium form of the zeolite can be further ion-exchanged to any other desired form. Ammonia calcination conditions include treatment in the ammonia atmosphere at temperatures between about 250° C. and about 600° C. and more preferably between about 250° C. and about 450° C. for times of 10 minutes to 5 hours. Optionally, the treatments can be carried out in multiple steps within this temperature range such that the total time in the ammonia atmosphere does not exceed 5 hours. Above 500° C., the treatments should be brief, less than a half hour and more preferably on the order of 5–10 minutes. Extended calcination times above 500° C. can lead to unintended dealumination along with the desired ammonium ion-exchange and are unnecessarily harsh as most organoammonium templates easily decompose at lower temperatures.

It should be pointed out that both calcination and steaming treatments not only remove organic cations, but can also dealuminate the zeolite. Thus, alternate embodiments of the invention include: a calcination treatment followed by acid extraction and steaming followed by acid extraction. A further embodiment of the invention comprises calcining or steaming the starting UZM-8 zeolite followed by an ion-exchange treatment. Of course an acid extraction can be carried out concurrently with, before or after the ion exchange.

The ion exchange conditions are the same as set forth above, namely a temperature of about 15° C. to about 100° C. and a time of about 20 minutes to about 50 hours. Ion exchange can be carried out with a solution comprising a cation (M1') selected from the group consisting of alkali metals, alkaline earth metals, rare earth metals, hydrogen ion, ammonium ion, and mixtures thereof. By carrying out this ion exchange, the M1 cation is exchanged for a secondary or different M1' cation. In a preferred embodiment, the UZM-8HS composition after the steaming or calcining steps is contacted with an ion exchange solution comprising an ammonium salt. Examples of ammonium salts include but are not limited to ammonium nitrate, ammonium chloride, ammonium bromide, and ammonium acetate. The ammonium ion containing solution can optionally contain a mineral acid such as but not limited to nitric, hydrochloric, sulfuric and mixtures thereof. The concentration of the mineral acid is that amount necessary to give a ratio of $H^+$ to $NH_4^+$ of 0 to 1. This ammonium ion exchange aids in removing any debris present in the pores after the steaming and/or calcination treatments.

It is apparent from the foregoing that, with respect to effective process conditions, it is desirable that the integrity of the zeolite crystal structure be substantially maintained throughout the dealumination process, and that the zeolite retains at least 50%, preferably at least 70 and more preferably at least 90% of its original crystallinity. A convenient technique for assessing the crystallinity of the products relative to the crystallinity of the starting material is the comparison of the relative intensities of the d-spacing of their respective X-ray powder diffraction patterns. The sum of the peak intensities, in arbitrary units above the background, of the starting material is used as the standard and is compared with the corresponding peak intensities of the products. When, for example, the numerical sum of the peak heights of the molecular sieve product is 85 percent of the value of the sum of the peak intensities of the starting zeolite, then 85 percent of the crystallinity has been retained. In practice it is common to utilize only a portion of the peaks for this purpose, as for example, five or six of the strongest peaks. Other indications of the retention of crystallinity are surface area and adsorption capacity. These tests may be preferred when the substituted metal significantly changes, e.g., increases, the absorption of x-rays by the sample or when peaks experience substantial shifts such as in the dealumination process.

After having undergone any of the dealumination treatments as described above, the UZM-8HS is usually dried and can be used in various processes as discussed below.

Applicants have found the properties of the UZM-8HS can be further modified by one or more additional treatment. These treatments include steaming, calcining or ion exchanging and can be carried out individually or in any combination. Some of these combinations include but are not limited to:

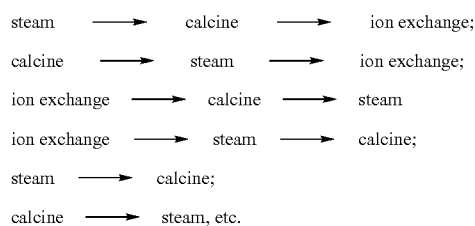

The dealumination treatment described above can be combined in any order to provide the zeolites of the invention although not necessarily with equivalent result. It should be pointed out that the particular sequence of treatments, e.g., AFS, acid extraction, steaming, calcining, etc can be repeated as many times as necessary to obtain the desired properties. Of course one treatment can be repeated while not repeating other treatments, e.g., repeating the AFS two or more times before carrying out steaming or calcining; etc. Finally, the sequence and/or repetition of treatments will determine the properties of the final UZM-8HS composition.

The UZM-8HS as prepared above is described by the empirical formula on an anhydrous basis of:

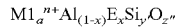

$$M1_a^{n+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and mixtures thereof, a is the mole ratio of M1 to (Al+E) and varies from about 0.05 to about 50, n is the weighted average valence of M1 and has a value of about +1 to about +3, E is an element selected from the group consisting of gallium, iron, boron, chromium, indium and mixtures thereof, x is the mole fraction of E and varies from 0 to 1.0, y' is the mole ratio of Si to (Al+E) and varies from greater than about 6.5 to virtually pure silica and z" is the mole ratio of O to (Al+E) and has a value determined by the equation:

$$z''=(a \cdot n+3+4 \cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 6.5 to 3,000 preferably greater than 10 to about 3,000; 6.5 to 10,000 preferably greater than 10 to about 10,000 and 6.5 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-8HS zeolite obtained after one or more of the above described treatments will have x-ray diffraction patterns which are different (and thus unique) from that of UZM-8. A list of the major peaks that are common to all the UZM-8HS materials is given in Table C.

TABLE C

UZM-8HS

| 2-θ | d(Å) | I/I₀% |
|---|---|---|
| 6.90–7.40 | 12.80–11.94 | w–vs |
| 8.15–8.85 | 10.84–9.98 | m–vs |
| 14.10–14.70 | 6.28–6.02 | w–vs |
| 19.40–20.10 | 4.57–4.41 | w–s |
| 22.00–22.85 | 4.04–3.89 | m–vs |
| 24.65–25.40 | 3.61–3.50 | w–m |
| 25.70–26.50 | 3.46–3.36 | w–vs |

The zeolites of this invention are capable of separating mixtures of molecular species based on the molecular size (kinetic diameter) or on the degree of polarity of the molecular species. When the separation of molecular species is based on molecular size, separation is accomplished by the smaller molecular species entering the intracrystalline void space while excluding larger species. The kinetic diameters of various molecules such as oxygen, nitrogen, carbon dioxide, carbon monoxide and various hydrocarbons are provided in D. W. Breck, Zeolite Molecular Sieves, John Wiley and Sons (1974) p. 636. The separation of hydrocarbons based on molecular size is a preferred application.

The hydrocarbon conversion processes in which the UZM-8, UZM-8HS and mixtures thereof can be used either as catalysts or catalyst supports are any of those well known in the art. These include without limitation cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Preferred hydrocarbon conversion processes are transalkylation of aromatics, alkylation of aromatics and isoparaffins and isomerization of aromatics.

For use in the hydrocarbon conversion processes described herein, the zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m²/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50–200° C. and subjected to a calcination procedure at a temperature of about 450-700° C. for a period of about 1 to about 20 hours. This treatment effects conversion of the hydrogel to the corresponding alumina matrix.

For isomerization of xylenes the catalyst will also include a platinum-group metal, including one or more of platinum, palladium, rhodium, ruthenium, osmium, and iridium, is an essential component of the present catalyst. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 5 mass-% and preferably from about 0.1 to about 2% of the final catalyst composite, calculated on an elemental basis.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the zeolite and binder. Yet another method of effecting a suitable metal distribution is by compositing the metal component with the binder prior to co-extruding the zeolite and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst composite of the present invention may contain a halogen component. The halogen component may be either fluorine, chlorine, bromine or iodine or mixtures thereof, with chlorine being preferred. The halogen component is generally present in a combined state with the inorganic-oxide support. The optional halogen component is preferably well dispersed throughout the catalyst and may comprise from more than 0.2 to about 15 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and, usually, calcined at a temperature of from about 400° to about 650° C. in an air atmosphere for a period of from about 1 to about 10 hours until the metallic compounds present are converted substantially to the oxide form. If desired, the optional halogen component may be adjusted by including a halogen or halogen-containing compound in the air atmosphere.

The resultant calcined composite optimally is subjected to a substantially water-free reduction step to insure a uniform and finely divided dispersion of the optional metallic components. The reduction optionally may be effected in situ. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

The feedstock to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include without limitation ortho-xylene, meta-xylene, para-xylene, ethylbenzene, ethyltoluenes, tri-methyl-benzenes, di-ethylbenzenes, tri-ethyl-benzenes, methylpropylbenzenes, ethylpropylbenzenes, di-isopropyl-benzenes, and mixtures thereof.

Isomerization of a $C_8$-aromatic mixture containing ethylbenzene and xylenes is a particularly preferred application for the zeolites of the invention. Generally such mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially (defined herein as a difference of at least 5 mass-% of the total $C_8$ aromatics) from the thermodynamic equilibrium concentration of that isomer at isomerization conditions. Usually the non-equilibrium mixture is prepared by removal of para- and/or ortho-xylene from a fresh $C_8$ aromatic mixture obtained from an aromatics-production process, and preferably the non-equilibrium mixture contains less than 5 mass-% para-xylene.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 0° to 600° C. or more, and preferably is in the range of from about 100° to 500° C. The pressure generally is from about 1 to 100 atmospheres absolute, preferably less than about 50 atmospheres. Sufficient catalyst is contained in the isomerization zone to provide a liquid hourly space velocity with respect to the hydrocarbon feed mixture of from about 0.1 to 30 $hr^{-1}$, and preferably 0.5 to 10 $hr^{-1}$. The hydrocarbon feed mixture optimally is reacted in admixture with hydrogen at a hydrogen/hydrocarbon mole ratio of about 0.5:1 to about 25:1 or more. Other inert diluents such as nitrogen, argon and light hydrocarbons may be present.

The reaction proceeds via the mechanism, described hereinabove, of isomerizing xylenes while reacting ethylbenzene to form a xylene mixture via conversion to and reconversion from naphthenes. The yield of xylenes in the product thus is enhanced by forming xylenes from ethylbenzene. The loss of $C_8$ aromatics through the reaction thus is low: typically less than about 4 mass-% per pass of $C_8$ aromatics in the feed to the reactor, preferably about 3 mass-% or less, and most preferably no more than about 2.5 mass-%.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. No. 3,626,020, U.S. Pat. No. 3,696,107, U.S. Pat. No. 4,039,599, U.S. Pat. No. 4,184,943, U.S. Pat. No. 4,381,419 and U.S. Pat. No. 4,402,832, incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The alkylation and preferably the monoalkylation of aromatic compounds involves reacting an aromatic compound with an olefin using the above described zeolitic catalyst. The olefins which can be used in the instant process are any of those which contain from 2 up to about 20 carbon atoms. These olefins may be branched or linear olefins and either terminal or internal olefins. Preferred olefins are ethylene, propylene and those olefins which are known as detergent range olefins. Detergent range olefins are linear olefins containing from 6 up through about 20 carbon atoms which have either internal or terminal double bonds. Linear olefins containing from 8 to 16 carbon atoms are preferred and those containing from 10 up to about 14 carbon atoms are especially preferred.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also can be substituted on the alkyl chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, etc.

The particular conditions under which the monoalkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. As a practical matter the pressure normally is in the range between about 200 and about 1,000 psig (1379–6985 kPa) but usually is in a range between about 300–600 psig (2069–4137 kPa). The alkylation of the alkylatable aromatic compounds with the olefins in the $C_2$–$C_{20}$ range can be carried out at a temperature of about 60° C. to about 400° C., and preferably from about 90° C. to about 250° C., for a time sufficient to form the desired product. In a continuous process this time can vary considerably, but is usually from about 0.1 to about 3 $hr^{-1}$ weight hourly space velocity with respect to the olefin. In particular, the alkylation of benzene with ethylene can be carried out at temperatures of about 200° C. to about 250° C. and the alkylation of benzene by propylene at a temperature of about 90° C. to about 200° C. The ratio of alkylatable aromatic compound to olefin used in the instant process will depend upon the degree of selective monoalkylation desired as well as the relative costs of the aromatic and olefinic components of the reaction mixture. For alkylation of benzene by propylene, benzene-to-olefin ratios may be as low as about 1 and as high as about 10, with a ratio of 2.5–8 being preferred. Where benzene is alkylated with ethylene a benzene-to-olefin ratio between about 1:1 and 8:1 is preferred. For detergent range olefins of $C_6$–$C_{20}$, a benzene-to-olefin ratio of between 5:1 up to as high as 30:1 is generally sufficient to ensure the desired monoalkylation selectivity, with a range between about 8:1 and about 20:1 even more preferred.

The zeolites of this invention can also be used to catalyze transalkylation. By "transalkylation" is meant that process where an alkyl group on one aromatic nucleus is intermolecularly transferred to a second aromatic nucleus. A preferred transalkylation process is one where one or more alkyl groups of a polyalkylated aromatic compound is transferred to a nonalkylated aromatic compound, and is exemplified by reaction of diisopropylbenzene with benzene to give two molecules of cumene. Thus, transalkylation often is utilized to add to the selectivity of a desired selective monoalkylation by reacting the polyalkylates invariably formed during alkylation with nonalkylated aromatic to form additional monoalkylated products. For the purposes of this process, the polyalkylated aromatic compounds are those formed in the alkylation of alkylatable aromatic compounds with olefins as described above, and the nonalkylated aromatic compounds are benzene, naphthalene, anthracene, and phenanthrene. The reaction conditions for transalkylation are similar to those for alkylation, with temperatures being in the range of about 100 to about 250°, pressures in the range of 100 to about 750 psig, and the molar ratio of unalkylated aromatic to polyalkylated aromatic in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene etc.

Hydrocracking conditions typically include a temperature in the range of 400° to 1200° F. (204–649° C.), preferably between 600° and 950° F. (316–510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (178–8,888 std. $m^3/m^3$), preferably between 2,000 and 30,000 scf per barrel of charge (355–5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-8 composition using feedstocks such as gas oils, heavy naphthas, deasphalted crude oil residua, etc. with gasoline being the principal desired product. Temperature conditions of 8500 to 1100° F., LHSV values of 0.5 to 10 and pressure conditions of from about 0 to 50 psig are suitable.

Alkylation of isoparaffins with olefins to produce alkylates suitable as motor fuel components is carried out at temperatures of –30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The structures of the UZM-8 and UZM-8HS zeolites of this invention were determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were either continuously scanned at 2° to 70° (2θ) or in a step mode from 4° to 35° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$," being the intensity of the strongest line or peak, and "I" being the intensity of each of the other peaks.

As will be understood by those skilled in the art the determination of the parameter 2θ is subject to both human and mechanical error, which in combination can impose an uncertainty of about +0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100%× $I/I_o$, the above designations are defined as:

w=0–15; m=15–60: s=60–80 and vs=80–100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLES

The following abbreviations will be used in the examples:

| | |
|---|---|
| Al(Oi-Pr)$_3$ | aluminum isopropoxide |
| Al(Osec-Bu)$_3$ | aluminum tri-sec-butoxide |
| DEDMAOH | diethyldimethylammonium hydroxide |
| ETMAOH | ethyltrimethylammonium hydroxide |
| HM(OH)$_2$ | hexamethonium dihydroxide |
| MTEAOH | methyltriethylammonium hydroxide |
| TEAOH | tetraethylammonium hydroxide |
| TEOS | tetraethylorthosilicate |
| TMACl | tetramethylammonium chloride |
| TPAOH | tetrapropylammonium hydroxide |

Example 1

This example illustrates how UZM-8 can be prepared in an alkali-free synthesis system from a homogenous solution. An aluminosilicate solution, designated Reagent A for this example, was prepared in the following manner. Al(Osec-Bu)$_3$ (97%), 4.63 g, was added to 159.63 g DEDMAOH (20% aq) with vigorous mixing, and to this reaction mixture there were added 189.78 g TEOS (98%) and 145.96 g deionized H$_2$O. The reaction mixture was homogenized for 2 hr with a high-speed mechanical stirrer, forming a homogenous aluminosilicate solution. This solution was then concentrated on a rotary evaporator, as the by-products of hydrolysis, ethanol and sec-butanol, and some water was removed. Elemental analysis of this aluminosilicate stock solution showed it to contain 7.86 wt. % Si and 0.16 wt. % Al.

Another aluminosilicate stock solution, designated Reagent B for this example, was prepared in the following manner. Al(Osec-Bu)$_3$ (97%), 60.91 g, was added to 280.00 g DEDMAOH (20% aq) with vigorous mixing, and to this mixture there were added 99.86 g TEOS (98%) and 59.23 g de-ionized H$_2$O. The reaction mixture was homogenized for 4.5 hr with a high-speed mechanical stirrer yielding a clear homogenous solution. Elemental analysis of the resulting aluminosilicate stock solution showed it to contain 3.54 wt. % Si and 1.80 wt. % Al.

A 79.59 g portion of Reagent A and a 15.63 g portion of Reagent B were combined and mixed well. With continuous mixing, 29.80 g DEDMAOH (20% aq) was added to the reaction mixture. The resulting solution was homogenized for 30 min before it was transferred to 2×125 mL Teflon™-lined autoclaves. The autoclaves were placed in an oven set at 150° C. and digested for 14 days and 19 days. The solid products were collected by centrifugation, washed with de-ionized water and dried at 95° C.

Powder x-ray diffraction analysis identified both of the isolated products as the material designated UZM-8. Characteristic lines in the diffraction pattern are shown in Table 1 below. Elemental analysis showed the product from the 14 day digestion to consist of the elemental mole ratios Si/Al=15.23, N/Al=1.55, and C/N=5.44. A portion of this material was calcined by ramping to 540° C. in N$_2$ for 4 hr followed by a 4 hr dwell in N$_2$. The stream was then switched to air and the sample was calcined for an additional 16 hr at 540° C. The BET surface area was found to be 472 m$^2$/g and the micropore volume was 0.11 cc/g.

TABLE 1

| 2-θ | d(Å) | I/I$_0$% |
|---|---|---|
| 2.91 | 30.29 | m |
| 6.58 | 13.42 | m |
| 7.26 | 12.17 | m |
| 8.67 | 10.19 | s |
| 13.45 | 6.58 | w |
| 14.61 | 6.06 | w |
| 20.01 | 4.43 | vs |
| 22.36 | 3.97 | s |
| 25.06 | 3.55 | w |
| 26.02 | 3.42 | s |
| 26.86 | 3.32 | m |
| 31.72 | 2.82 | w |
| 33.44 | 2.68 | w |
| 37.86 | 2.37 | w |
| 46.42 | 1.95 | w |
| 48.61 | 1.87 | w |
| 51.90 | 1.76 | w |
| 65.48 | 1.42 | w |

Example 2

An aluminosilicate stock solution was prepared in the following manner. While mixing vigorously, 28.03 g of Al(Osec-Bu)$_3$ (97%) was added to 644.36 g DEDMAOH (20% aq). After mixing for 5 min, 324.76 g colloidal silica (Ludox™ AS-40, 40% SiO$_2$) was slowly added. A 2.85 g portion of deionized H$_2$O was then added. The mixture was homogenized for 20 min before transferring to two 1 L Teflon bottles. The Teflon bottles were placed in a 100° C. oven and the mixture was aged for 67 hr. After the aging step, the resulting clear aluminosilicate solutions were recombined and analyzed. Elemental analysis indicated this aluminosilicate stock solution contained 6.59 wt. % Si and 0.34 wt. % Al.

A 60.47 g portion of the above aluminosilicate solution was transferred to a Teflon-lined autoclave. The autoclave was placed in an oven set at 150° C. and the reaction mixture was digested for 7 days. The solid product was collected by centrifugation, washed with de-ionized water, and dried at room temperature.

The product was identified as UZM-8 by powder x-ray diffraction analysis. A listing of the x-ray diffraction lines characteristic of the sample are given below in Table 2. Elemental analysis showed the product to consist of the elemental mole ratios Si/Al=16.18, N/Al=2.14, and C/N=5.62. A portion of the material was calcined by ramping to 538° C. in N$_2$ for 3 hr followed by a 5 hr dwell in N$_2$. The stream was then switched to air and the sample was calcined an additional 16 hr at 538° C. The BET surface area was found to be 370 m$^2$/g and the micropore volume was 0.12 cc/g.

TABLE 2

| 2-θ | d(Å) | I/I$_0$% |
|---|---|---|
| 7.22 | 12.24 | s |
| 8.58 | 10.30 | s |
| 20.01 | 4.43 | s |
| 22.29 | 3.99 | vs |
| 25.12 | 3.54 | m |
| 26.04 | 3.42 | vs |

Example 3

A 55.14 g portion of the aluminosilicate stock solution prepared in Example 2 was weighed into a beaker. Separately, 0.79 g TMACl was dissolved in 4.08 g de-ionized $H_2O$. This TMACl solution was added to the aluminosilicate solution and thoroughly mixed with a high-speed stirrer. The reaction mixture, which remained a solution, was then transferred to a Teflon-lined autoclave. The autoclave was placed in an oven set at 150° C. and the reaction mixture was digested for 7 days. The solid product was collected by centrifugation, washed with de-ionized water, and dried at room temperature.

Powder x-ray diffraction analysis showed the product to be the material designated UZM-8. Characteristic diffraction lines for the product are shown in Table 3. Elemental analyses showed the product to consist of the elemental mole ratios Si/Al=14.38, Na/Al=0.02, N/Al=2.02, and C/N=5.58. The sodium came from the silica source. A portion of the material was calcined by ramping to 538° C. in $N_2$ for 3 hr followed by a 5 hr dwell in $N_2$. The stream was then switched to air and the sample was calcined for an additional 16 hr at 538° C. The BET surface area was found to be 370 $m^2/g$ and the micropore volume was 0.12 cc/g.

TABLE 3

| 2-θ | d(Å) | $I/I_0$% |
|---|---|---|
| 3.04 | 29.00 | w |
| 6.68 | 13.22 | m |
| 7.22 | 12.23 | m |
| 8.70 | 10.16 | m |
| 14.63 | 6.05 | w |
| 19.98 | 4.44 | vs |
| 22.43 | 3.96 | vs |
| 25.03 | 3.55 | w |
| 26.02 | 3.42 | s |
| 26.57 | 3.35 | s |
| 31.55 | 2.83 | w |
| 33.35 | 2.68 | w |
| 37.74 | 2.38 | w |
| 46.33 | 1.96 | w |
| 48.80 | 1.86 | w |
| 51.81 | 1.76 | w |
| 65.46 | 1.42 | w |

Example 4

An aluminosilicate stock solution was prepared in the following manner. Al(Osec-Bu)$_3$ (97%), 6.44 g, was added to 151.18 g DEDMAOH (20% aq) with vigorous mixing. With continuous mixing, 161.76 g TEOS (98%) and 80.62 g deionized $H_2O$ were added to the reaction mixture. The reaction mixture was homogenized for 1.5 hr with a high-speed mechanical stirrer. The solution was then concentrated with a rotary evaporator to remove some of the alkoxide hydrolysis products, ethanol and sec-butanol, and some water. Elemental analysis showed the aluminosilicate stock solution to contain 8.66 wt. % Si and 0.27 wt. % Al.

A 24.24 g portion of DEDMAOH (20% aq) was added to 43.69 g portion of the above aluminosilicate stock solution and mixed well. A solution comprised of 0.51 g NaCl and 1.56 g deionized $H_2O$ was prepared and added to the reaction mixture while mixing. The reaction mixture was homogenized for 40 min yielding a clear homogenous solution which was then transferred to a Teflon-lined autoclave, which was placed in an oven heated to 150° C. and the reaction mixture was digested for 7 days. The solid product was collected by centrifugation, washed with de-ionized water, and dried at 95° C.

Powder x-ray diffraction analysis indicated the product to be the material designated UZM-8. The characteristic diffraction lines for this sample are given in Table 4 below. Elemental analysis showed the product to consist of the elemental mole ratios Si/Al=23.91, Na/Al=0.42, N/Al=3.16 and C/N=5.46. A portion of the material was calcined by ramping to 540° C. in $N_2$ for 4 hr followed by a 4 hr dwell in $N_2$. The stream was then switched to air and the sample was held for an additional 16 hr at 540° C. The BET surface area was found to be 356 $m^2/g$ and the micropore volume was 0.12 cc/g.

TABLE 4

| 2-θ | d(Å) | $I/I_0$% |
|---|---|---|
| 3.08 | 28.62 | m |
| 6.68 | 13.22 | m |
| 7.21 | 12.25 | m |
| 8.76 | 10.08 | m |
| 14.70 | 6.02 | w |
| 20.11 | 4.41 | m |
| 22.52 | 3.94 | vs |
| 25.14 | 3.54 | m |
| 26.06 | 3.42 | m–s |
| 26.86 | 3.32 | m |
| 29.09 | 3.07 | m |
| 33.44 | 2.68 | w |
| 46.31 | 1.96 | w |
| 48.44 | 1.88 | w |
| 65.56 | 1.42 | w |

Example 5

An aluminosilicate reaction mixture was prepared in the following manner. Al(Osec-Bu)$_3$ (97%), 66.51 g, was added to 918.29 g of DEDMAOH, (20% aq) with vigorous stirring. To this mixture, 208.95 g precipitated silica, (Ultrasil™ VN SP3, 89% $SiO_2$) was added with continuous mixing. A solution of 37.2 g $Na_2SO_4$ in 169.05 g deionized $H_2O$ was prepared and added to the previous mixture and homogenized for 10 min. A 1.7 g portion of UZM-8 seed was added to the mixture, followed by an additional 20 min of mixing. A 1077.3 g portion of this final reaction mixture was transferred to a 2-L Teflon-lined autoclave. The autoclave was placed in an oven set at 150° C. and the reaction mixture was digested quiescently for 10 days. The solid product was collected by filtration, washed with de-ionized water, and dried at 95° C.

The product was identified as UZM-8 by powder x-ray diffraction analysis. Table 5 below shows the characteristic diffraction lines for the product. Elemental analysis revealed the composition of the isolated product to consist of the elemental mole ratios Si/Al=9.96, Na/Al=0.26, N/Al=1.23, and C/N=4.83. A portion of the material was calcined by ramping to 538° C. in $N_2$ for 3 hr followed by a 4 hr dwell in $N_2$. The stream was then switched to air and the sample was calcined for another 15 hr at 538° C. The calcined sample was then ammonium ion-exchanged to remove the alkali cations. The sample was then reactivated by heating to 500° C. in air and holding at that temperature for 2 hr. The BET surface area was found to be 343 $m^2/g$ and the micropore volume was 0.14 cc/g.

TABLE 5

| 2-θ | d(Å) | I/I₀% |
|---|---|---|
| 3.00 | 29.39 | s |
| 6.71 | 13.17 | m |
| 7.16 | 12.34 | m |
| 8.52 | 10.37 | vs |
| 13.06 | 6.77 | w |
| 14.39 | 6.15 | w |
| 15.80 | 5.60 | w |
| 20.01 | 4.43 | m |
| 22.18 | 4.00 | vs |
| 25.03 | 3.55 | m |
| 25.98 | 3.43 | vs |
| 26.95 | 3.31 | m |
| 28.87 | 3.09 | w–m |
| 31.43 | 2.84 | w |
| 33.35 | 2.68 | w |
| 37.65 | 2.39 | w |
| 44.50 | 2.03 | w |
| 46.15 | 1.97 | w |
| 46.36 | 1.96 | w |
| 48.43 | 1.88 | w |
| 51.64 | 1.77 | w |
| 61.04 | 1.52 | w |
| 65.34 | 1.43 | w |

TABLE 6

| 2-θ | d(Å) | I/I₀% |
|---|---|---|
| 3.19 | 27.69 | w |
| 6.70 | 13.19 | s |
| 7.16 | 12.33 | m |
| 8.90 | 9.93 | w |
| 13.37 | 6.61 | w |
| 14.58 | 6.07 | w |
| 20.06 | 4.42 | vs |
| 22.41 | 3.96 | m |
| 25.06 | 3.55 | w |
| 26.04 | 3.42 | s |
| 26.59 | 3.35 | m |
| 29.28 | 3.05 | w |
| 33.58 | 2.67 | w |
| 37.90 | 2.37 | w |
| 44.77 | 2.02 | w |
| 46.25 | 1.96 | w |
| 48.60 | 1.87 | w |
| 51.90 | 1.76 | w |
| 65.34 | 1.43 | w |

Example 6

An aluminosilicate stock solution was prepared in the following manner. Al(Osec-Bu)$_3$ (95+%), 17.28 g, was added to 719.57 g ETMAOH (12.8%) with vigorous stirring. To this mixture, 260.12 g colloidal silica, (Ludox AS-40, 40% SiO$_2$) was added, followed by the addition of 3.03 g distilled water. The reaction mixture was homogenized for ½ hr with a high-speed mechanical stirrer, and then aged in Teflon bottles overnight at 98° C. After the aging step, the reaction mixture was a homogenous clear solution. Elemental analysis indicated the aluminosilicate stock solution had a silicon content of 4.93 wt. % and 0.22 wt. % Al.

With vigorous mixing, a 154.21 g portion of the above reaction mixture was combined with a solution consisting of 3.67 g NaCl and 52.11 g de-ionized H$_2$O. The reaction mixture was homogenized for 25 min with a high-speed mechanical stirrer. A 188.86 g portion of the above reaction mixture was distributed among three 125 mL Teflon-lined autoclaves. The autoclaves were placed in an oven set at 150° C. and the reaction mixtures digested for 7 days. The solid products were collected by centrifugation, washed with de-ionized water, and dried at 95° C.

Powder x-ray diffraction analysis showed that all three products exhibited the lines characteristic of the material designated UZM-8. Based on the similarity of the diffraction patterns, the three samples were combined. Characteristic diffraction lines for the products are shown in Table 6. Elemental analyses showed the composite sample to consist of the elemental mole ratios Si/Al=12.97, Na/Al=0.37, N/Al=1.77, and C/N=4.92. A portion of this material was ammonium ion-exchanged to remove the alkali cations. That material was then calcined by ramping to 540° C. in N$_2$ for 4 hr followed by a 4 hr dwell in N$_2$. The stream was then switched to air and the sample was held for an additional 15 hr at 540° C. The BET surface area was found to be 360 m$^2$/g and the micropore volume was 0.14 cc/g.

Example 7

An aluminosilicate reaction mixture was prepared in the following manner. Al(Osec-Bu)$_3$ (97%), 8.11 g, was added to 133.22 g DEDMAOH (20% aq) with vigorous mixing. With continuous mixing, 43.30 g precipitated silica (Ultrasil VN SP3, 89% SiO$_2$) was added. Separately, 1.19 g KCl and 3.61 g TMACl were dissolved in 10.56 g de-ionized H$_2$O. The salt solution was then added to the aluminosilicate reaction mixture. The reaction mixture was homogenized for 15 min with a high-speed mechanical stirrer. A 46.4 g portion of the reaction mixture was transferred to a 100 mL Parr stainless steel stirred autoclave. The autoclave was heated to 150° C. and maintained at that temperature for 145 hr with continuous stirring. The resultant solid product was collected by centrifugation, washed with de-ionized water, and dried at 95° C.

Powder x-ray diffraction analysis identified the product as the material designated UZM-8. Characteristic lines in the diffraction pattern of this sample are given in Table 7 below. Elemental analysis showed the product to consist of the elemental mole ratios Si/Al=16.34, K/Al=0.14, N/Al=1.88. A portion of the material was calcined by ramping to 540° C. in N$_2$ for 4 hr followed by a 4 hr dwell in N$_2$. The stream was then switched to air and the sample was held for an additional 16 hr at 540° C. The BET surface area was found to be 283 m$^2$/g and the micropore volume was 0.08 cc/g.

TABLE 7

| 2-θ | d(Å) | I/I₀% |
|---|---|---|
| 6.55 | 13.49 | w |
| 7.13 | 12.38 | m |
| 8.64 | 10.23 | m |
| 20.01 | 4.43 | s |
| 22.47 | 3.95 | vs |
| 25.04 | 3.55 | w |
| 25.94 | 3.43 | m |
| 26.61 | 3.35 | w |

Example 8

An aluminosilicate stock solution was prepared in the following manner. With vigorous mixing, 28.03 g of Al(Osec-Bu)$_3$ (97%) was added to 644.36 g DEDMAOH (20% aq). After mixing for 5 min, 324.76 g colloidal silica (Ludox AS-40, 40 wt. % $SiO_2$) was slowly added. A 2.85 g portion of de-ionized $H_2O$ was then added. The mixture was homogenized for 20 min before transferring to two 1 L Teflon bottles. The Teflon bottles were placed in a 100° C. oven and the mixture was aged for 67 hr. After the aging step, the reaction mixture was a homogenous clear solution. Elemental analysis indicated the aluminosilicate stock solution contained 6.59 wt. % Si and 0.34 wt. % Al.

A solution comprised of 1.31 g TMACl, 0.25 g LiCl and 6.78 g deionized $H_2O$ was prepared. This salt solution was added to a 91.67 g portion of the aluminosilicate stock solution prepared above. The resulting mixture was homogenized for 15 min before transferring a 19.87 g portion to a Teflon-lined autoclave. The autoclave was placed in an oven set at 150° C. and the reaction mixture digested for 7 days. The solid product was collected by centrifugation, washed with de-ionized water and dried at room temperature.

Powder x-ray diffraction analysis indicated the product to be the material designated UZM-8. Characteristic diffraction lines for the product are given below in Table 8. Elemental analyses showed the product to consist of the elemental mole ratios Si/Al=16.22, Li/Al=0.31, N/Al=3.52 and C/N=5.54. A portion of the material was calcined by ramping to 540° C. in $N_2$ for 4 hr followed by a 4 hr dwell in $N_2$. The stream was then switched to air and the sample was calcined for an additional 16 hr at 540° C. The BET surface area was found to be 403 $m^2/g$ and the micropore volume was 0.15 cc/g.

TABLE 8

| 2-θ | d(Å) | $I/I_0$% |
|---|---|---|
| 3.06 | 28.82 | s |
| 6.70 | 13.19 | s |
| 7.21 | 12.26 | s |
| 8.80 | 10.04 | m |
| 13.55 | 6.53 | w |
| 14.74 | 6.00 | w |
| 20.01 | 4.43 | vs |
| 22.46 | 3.96 | vs |
| 25.06 | 3.55 | m |
| 26.04 | 3.42 | m |
| 26.81 | 3.32 | w |
| 29.08 | 3.07 | w |
| 33.53 | 2.67 | w |
| 46.27 | 1.96 | w |
| 48.66 | 1.87 | w |
| 51.83 | 1.76 | w |
| 65.34 | 1.43 | w |

Example 9

An aluminosilicate stock solution mixture was prepared in the following manner. In a beaker, 187.87 g DEDMAOH (20% aq) was combined with 209.98 g MTEAOH hydroxide (20% aq). While mixing vigorously, 12.81 g Al(Osec-Bu)$_3$ (97%) was added to the beaker. With continuous mixing, 189.37 g colloidal silica (Ludox AS-40, 40 wt. % $SiO_2$) was added. The reaction mixture was homogenized for 30 min before transferring to a 1 L Teflon bottle. The Teflon bottle was placed in a 95° C. oven and the reaction mixture was aged for 66 hr. at 95° C. After the aging step the reaction mixture was a clear homogenous solution. Elemental analysis indicated that this aluminosilicate stock solution contained 6.06 wt. % Si and 0.24 wt. % Al.

A solution comprised of 2.87 g NaCl and 8.80 g deionized $H_2O$ was added to a 113.32 g portion of the aluminosilicate stock solution. The reaction mixture was then homogenized for 20 min with a high-speed stirrer. A 20.59 g portion of the reaction mixture was transferred to a Teflon-lined autoclave. The autoclave was placed in an oven set at 150° C. and the reaction mixture was digested for 10 days. The solid product was collected by centrifugation, washed with de-ionized water, and dried at 95° C.

Powder x-ray diffraction analysis indicated the product to be the material designated UZM-8. Characteristic diffraction lines for the product are listed in Table 9 below. Elemental analysis showed the product consisted of the elemental mole ratios Si/Al=17.63, Na/Al=1.82, N/Al=2.86 and C/N=7.19. A portion of this material was ammonium ion-exchanged to remove the alkali cations. That material was then calcined by ramping to 540° C. in $N_2$ for 4 hr followed by a 4 hr dwell in $N_2$. The stream was then switched to air and the sample was calcined for an additional 15 hr at 540° C. The BET surface area was found to be 328 m 2/g and the micropore volume was 0.12 cc/g.

TABLE 9

| 2-θ | d(Å) | $I/I_0$% |
|---|---|---|
| 2.86 | 30.91 | vs |
| 6.63 | 13.32 | w |
| 7.14 | 12.37 | m |
| 8.77 | 10.08 | w–m |
| 13.54 | 6.54 | w |
| 14.75 | 6.00 | w |
| 16.11 | 5.50 | w |
| 19.89 | 4.46 | vs |
| 22.42 | 3.96 | s |
| 25.00 | 3.56 | m |
| 25.96 | 3.43 | s |
| 26.60 | 3.35 | m |
| 33.19 | 2.70 | w |
| 37.80 | 2.38 | w |
| 46.13 | 1.97 | w |
| 51.80 | 1.76 | w |
| 65.25 | 1.43 | w |

Example 10

An aluminosilicate stock solution was prepared in the following manner. With vigorous mixing, 13.75 g of Al(Osec-Bu)$_3$ (97%) was added to 221.27 g DEDMAOH (20% aq). After mixing for 5 min, 159.31 g colloidal silica (Ludox AS-40, 40% $SiO_2$) was slowly added. A 5.66 g portion of de-ionized $H_2O$ was then added. The mixture was homogenized for 20 min before transferring to a 1 L Teflon bottle. The Teflon bottle was placed in a 100° C. oven and the mixture was aged for 41 hr. After the aging step, the reaction mixture was a clear homogenous solution. Elemental analysis indicated the aluminosilicate stock solution contained 8.45 wt. % Si and 0.44 wt. % Al.

A 56.65 g portion of the above aluminosilicate stock solution was weighed into a beaker. Separately, a solution comprised of 0.77 g CsCl, 1.04 g TMACl and 1.53 g de-ionized $H_2O$ was prepared. While stirring, the salt solution was added to the aluminosilicate solution. The reaction mixture was homogenized for 20 min before transferring a 20.01 g portion to a Teflon-lined autoclave. The autoclave was placed in an oven set at 175° C. and the reaction mixture digested for 7 days. The solid product was collected by centrifugation, washed with de-ionized water and dried at room temperature.

Powder x-ray diffraction indicated the product to be the material designated UZM-8. Characteristic diffraction lines for the product are listed in Table 10. Elemental analysis showed the product to consist of the elemental mole ratios Si/Al=18.2, Cs/Al=0.35, N/Al=2.48 and C/N=4.98.

TABLE 10

| 2-θ | d(Å) | I/I₀% |
|---|---|---|
| 7.26 | 12.17 | m |
| 8.72 | 10.13 | w |
| 19.94 | 4.45 | s |
| 22.53 | 3.94 | vs |
| 25.02 | 3.56 | w |
| 26.08 | 3.41 | m |
| 26.79 | 3.32 | m |

Example 11

An aluminosilicate stock solution was prepared by adding 15.39 g of Al(Osec-Bu)₃ (95+%) to a combination of 99.79 g of a TPAOH solution (40%) and 349.93 g of a DEDMAOH solution (20%) with vigorous stirring. This was followed by the addition of 235.18 g of colloidal silica, (Ludox AS-40, 40% SiO₂). The reaction mixture was homogenized for 50 minutes with a high-speed mechanical stirrer, and then aged in a Teflon bottle overnight at 95° C. After the aging step, the reaction mixture was a clear, homogenous solution. Elemental analysis indicated the aluminosilicate stock solution contained 6.35 wt. % Si.

A 159.39 g portion of the aluminosilicate stock solution prepared above was treated with a solution consisting of 4.15 g of NaCl dissolved in 16.50 g distilled water while mixing vigorously. After 20 min of homogenization, the reaction mixture was distributed among 6 Teflon-lined autoclaves and two Teflon bottles. The reaction mixtures in the autoclaves were reacted at 125° C. and 150° C. for 10 and 14 days and at 175° C. for 3 and 7 days and the mixtures in the bottles were reacted at 100° C. for 14 and 21 days. All reactions were carried out at autogenous pressures. The solid products were isolated by centrifugation, washed with de-ionized water, and dried at 50° C.

The product of the reaction at 125° C. for 14 days exhibited the x-ray diffraction pattern of UZM-8. Representative diffraction lines for this product are listed in Table 11. Elemental analysis of the same product indicated the elemental mole ratios of Si/Al=12.57; Na/Al=0.37; N/Al=1.79; and C/N=7.37. A portion of the product was calcined under a flow of nitrogen for 4 hours at 540° C. and then in air for an additional 16 hours at 540° C. The calcined product had a BET surface area of 391 m²/g and a micropore volume of 0.11 cc/g.

TABLE 11

| 2-θ | d(Å) | I/I₀% |
|---|---|---|
| 6.53 | 13.54 | m |
| 7.11 | 12.43 | m |
| 8.58 | 10.30 | vs |
| 13.06 | 6.77 | w |
| 14.55 | 6.08 | w |
| 19.88 | 4.46 | s–vs |
| 22.35 | 3.97 | s |
| 24.90 | 3.57 | w |
| 25.89 | 3.44 | vs |
| 26.96 | 3.30 | m |
| 33.09 | 2.71 | w |
| 37.75 | 2.38 | w |
| 46.26 | 1.96 | w |
| 48.68 | 1.87 | w |

TABLE 11-continued

| 2-θ | d(Å) | I/I₀% |
|---|---|---|
| 51.81 | 1.76 | w |
| 65.26 | 1.43 | w |

Example 12

An aluminosilicate stock solution was prepared by adding 15.16 g of Al(Osec-Bu)₃ (95+%) to a mixture of 396.02 g DEDMAOH solution (20%) and 56.43 g TPAOH solution (40%) with vigorous stirring. Next, 232.87 g colloidal silica (Ludox AS-40, 40% SiO₂) was added and the reaction mixture was homogenized for another 1.5 hours. This mixture was aged overnight in a Teflon bottle at 95° C. After the aging step, the reaction mixture was a clear, homogenous solution. Elemental analysis indicated the aluminosilicate stock solution contained 6.34 wt. % Si.

A portion of this aluminosilicate stock solution, 125.26 g, was treated with a NaCl solution (3.27 g NaCl in 11.48 g water) while mixing vigorously. After homogenization, a portion of the resulting mixture was transferred to a Teflon-lined autoclave and digested at 125° C. for 14 days. The solid product was recovered by centrifugation, washed with de-ionized water, and dried at 50° C.

Powder X-ray diffraction indicated the product formed to be UZM-8. Representative diffraction lines for the product are given in Table 12 below. Elemental analyses indicated the product to consist of the elemental mole ratios Si/Al=13.60; Na/Al=0.80; N/Al=3.02; and C/N=7.82. A portion of the product was calcined under a flow of nitrogen for 4 hours at 540° C. and then in air for an additional 16 hours at 540° C. The calcined product had a BET surface area of 312 m²/g and a micropore volume of 0.10 cc/g.

TABLE 12

| 2-θ | d(Å) | I/I₀% |
|---|---|---|
| 2.86 | 30.87 | w |
| 6.40 | 13.80 | m |
| 7.08 | 12.48 | m |
| 8.58 | 10.30 | vs |
| 12.73 | 6.95 | w |
| 14.74 | 6.01 | m |
| 19.80 | 4.48 | vs |
| 22.20 | 4.00 | vs |
| 24.94 | 3.57 | m |
| 25.88 | 3.44 | vs |
| 26.86 | 3.32 | m–s |
| 33.26 | 2.69 | w |
| 36.31 | 2.47 | w |
| 37.66 | 2.39 | w |
| 46.16 | 1.97 | w |
| 48.43 | 1.88 | w |
| 51.90 | 1.76 | w |
| 65.34 | 1.43 | w |

Example 13

To 102.89 g of the same aluminosilicate stock solution employed in example 12, a NaCl solution (2.67 g NaCl in 9.42 g water) was added with vigorous stirring. The resulting mixture was transferred to six Teflon™-lined autoclaves and the mixtures reacted at 115° C. for 4, 10, 15, 20, and 25 days. The solid products were recovered by centrifugation, washed with de-ionized water, and dried at 60° C.

The product formed at 115° C. for 25 days was identified as UZM-8 by powder x-ray diffraction. Representative diffraction lines in the pattern are given in Table 13. The sample was analyzed and found to have elemental mole ratios of Si/Al=11.31; Na/Al=0.95; N/Al=3.03; and C/N=7.85. A portion of the product was calcined under a flow of nitrogen for 4 hours at 540° C. and then in air for 16 hours at 540° C., and then characterized by nitrogen adsorption. The BET surface area was 355 m²/g and the micropore volume was 0.091 cc/g.

TABLE 13

| 2-θ | d(Å) | I/I₀% |
|---|---|---|
| 7.04 | 12.55 | w |
| 8.45 | 10.40 | m |
| 19.97 | 4.44 | m |
| 22.25 | 3.99 | vs |
| 24.85 | 3.58 | w |
| 25.78 | 3.45 | vs |

Example 14

A Na gallate solution (9.91% Ga, 6.31% Na) was prepared. A 4.78 g portion of the Na gallate solution was combined with 44.84 g DEDMAOH (20% aq) and mixed with a mechanical stirrer. With continuous mixing, 19.58 g Ludox AS-40 and 0.80 g deionized H₂O were added to the reaction mixture. The reaction mixture was mixed for 20 min and then transferred to a 125 mL Teflon-lined autoclave. The autoclave was placed in an oven set at 150° C. and digested for 10 days at autogenous pressure. The solid product was collected by filtration, washed and dried at 95° C.

Characterization by powder x-ray diffraction identified the product as UZM-8. Characteristic diffraction lines for the product are given in table 14. By elemental analysis, it was determined that the material consisted of the elemental mole ratios Si/Ga=12.65, Na/Ga=0.14, N/Ga=1.38, and C/N=5.7. A portion of this material was ammonium ion-exchanged to remove the alkali cations. That material was then calcined by ramping to 540° C. in N₂ for 4 hr followed by a 4 hr dwell in N₂. The stream was then switched to air and the sample was held 16 hr at 540° C. in air. The BET surface area was found to be 333 m²/g and the micropore volume was 0.14 cc/g.

TABLE 14

| 2-θ | d(Å) | I/I₀% |
|---|---|---|
| 3.12 | 28.31 | vs |
| 6.68 | 13.22 | s |
| 7.12 | 12.41 | vs |
| 8.63 | 10.24 | m |
| 12.81 | 6.90 | w |
| 15.78 | 5.61 | w |
| 19.96 | 4.45 | s |
| 22.24 | 3.99 | s |
| 24.98 | 3.56 | m |
| 25.92 | 3.43 | vs |
| 26.60 | 3.35 | m |
| 29.02 | 3.07 | w |
| 31.49 | 2.84 | w |
| 33.37 | 2.68 | m |
| 36.26 | 2.48 | w |
| 37.67 | 2.39 | w |
| 44.67 | 2.03 | w |
| 46.21 | 1.96 | w |

TABLE 14-continued

| 2-θ | d(Å) | I/I₀% |
|---|---|---|
| 48.48 | 1.88 | w |
| 51.90 | 1.76 | w |
| 65.22 | 1.43 | w |

Example 15

A first aluminosilicate stock solution was prepared by dissolving 34.76 g of aluminum sec-butoxide (95+%) in 337.83 g hexamethonium dihydroxide solution (19.75%), followed by the addition of 360.24 g de-ionized water while stirring vigorously. Then 300.0 g of tetraethylorthosilicate (98%) was added and the resulting mixture homogenized for 2 hours with a high-speed mechanical stirrer. The resulting solution was transferred to a rotary evaporator to remove alcohol from the hydrolysis of the alkoxides and sent for analysis after cooling. The analysis indicated a Si content of 5.27 wt. %.

A second aluminosilicate stock solution was prepared by dissolving 9.93 g of aluminum sec-butoxide (95+%) in 295.59 g hexamethonium dihydroxide (19.75%) solution, followed by the addition of 413.46 g de-ionized water while stirring vigorously. Then 300.0 g of tetraethylorthosilicate (98%) was added and the resulting mixture homogenized for 2 hours with a high-speed mechanical stirrer. The resulting solution was transferred to a rotary evaporator to remove alcohol from the hydrolysis of the alkoxides and sent for analysis after cooling. The analysis indicated a Si content of 5.51 wt. %.

The synthesis of the zeolite was carried out as follows. A volume of 694 µL of the first aluminosilicate stock solution was pipetted to a teflon reactor. Next, a volume of 356 µL of the second aluminosilicate stock solution was pipetted to the same teflon reactor while mixing on an orbital shaker. Next 20 µL of hexamethonium dihydroxide solution (19.75%) were added, followed by 30 µL of strontium nitrate solution (22.7%). The teflon reactor was then sealed and the reaction mixture homogenized vigorously for an hour and then inserted into an autoclave which was placed into an oven for 120 hours at 175° C. The resulting product was washed, centrifuged, and dried overnight at 75° C.

The x-ray diffraction pattern exhibited the lines characteristic of the material designated UZM-8. Characteristic lines in the diffraction pattern are given in Table 15.

TABLE 15

| 2-θ | d(Å) | I/I₀% |
|---|---|---|
| 6.50 | 13.59 | vs |
| 7.05 | 12.53 | m |
| 8.67 | 10.19 | m |
| 12.80 | 6.91 | w |
| 14.61 | 6.06 | w |
| 20.00 | 4.44 | s |
| 22.05 | 4.03 | m |
| 24.95 | 3.57 | m |
| 25.95 | 3.43 | s |
| 26.65 | 3.34 | m |
| 33.51 | 2.67 | w |

Example 16

Figure 1B:
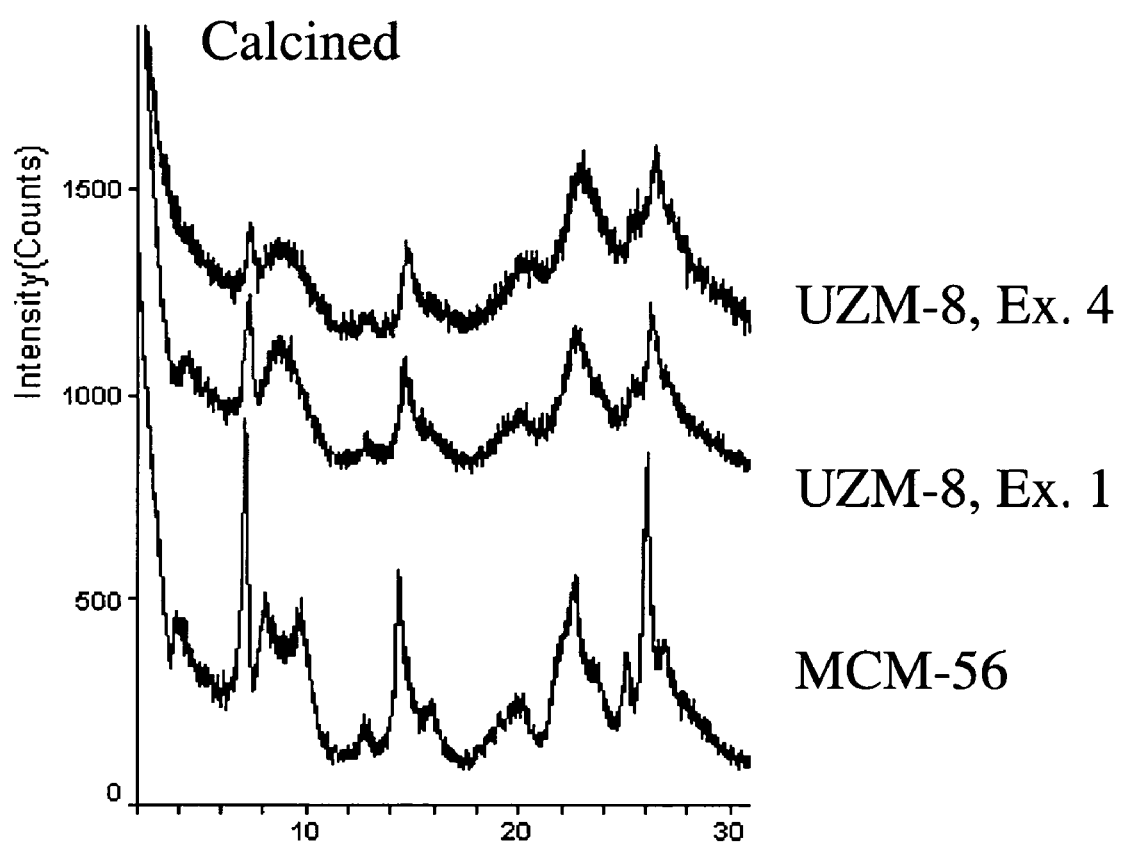
FIG. 1b presents x-ray diffraction patterns for calcined UZM-8 compositions of examples 1 and 4, and for zeolite MCM-56.

This example presents a comparison of MCM-56 versus UZM-8, both as-synthesized and calcined. MCM-56 was prepared according to Example 8 of U.S. Pat. No. 5,827,491. A sample withdrawn at 60 hrs was washed dried and calcined at 540° C. for 4 hr in $N_2$ and 16 hr in air. The UZM-8 samples from Examples 1 and 4 were also calcined using the same program. The diffraction lines for each of the calcined samples are given below in Table 16. FIG. 1a shows the x-ray diffraction patterns for three as-synthesized samples, while the diffraction patterns for the corresponding calcined patterns are shown in FIG. 1b. Both the Figures and Table 16 show that UZM-8 has a different diffraction pattern and thus a different structure from MCM-56.

TABLE 16

Calcined MCM-56 and UZM-8

| MCM-56 | | | Example 1 | | | Example 4 | | |
|---|---|---|---|---|---|---|---|---|
| 2-θ | d(Å) | I/I₀% | 2-θ | d(Å) | I/I₀% | 2-θ | d(Å) | I/I₀% |
| 4.10 | 21.52 | m | 4.38 | 20.17 | m | | | |
| 7.10 | 12.44 | vs | 7.28 | 12.14 | m | 7.34 | 12.03 | m |
| 8.04 | 10.98 | m | 8.76 | 10.08 | s | 8.91 | 9.92 | m |
| 9.76 | 9.06 | vs | | | | | | |
| 12.69 | 6.97 | w | 12.79 | 6.92 | w | 12.84 | 6.89 | w |
| 14.34 | 6.17 | vs | 14.60 | 6.06 | vs | 14.70 | 6.02 | vs |
| 15.89 | 5.57 | m | 16.08 | 5.51 | w | 15.88 | 5.58 | w |
| 19.93 | 4.45 | m | 19.91 | 4.46 | m | 20.19 | 4.40 | w |
| 22.56 | 3.94 | vs | 22.66 | 3.92 | s | 22.82 | 3.89 | vs |
| 23.56 | 3.77 | m | 25.35 | 3.51 | w | | | |
| 25.00 | 3.56 | m | | | | | | |
| 26.04 | 3.42 | vs | 26.31 | 3.38 | m | 26.40 | 3.37 | vs |
| 26.88 | 3.31 | m | 27.04 | 3.31 | m | | | |

Example 17

UZM-8, MCM-56, and MCM-22 were compared in decane hydroconversion tests. The UZM-8 used was prepared by the procedure given in Example 5 above, the MCM-56 was prepared according to Example 1 of U.S. Pat. No. 5,362,697, while MCM-22 was prepared according to Example 4 of U.S. Pat. No. 4,954,325, except that the digestion time in the autoclave was shortened to 99 hr at 143° C. The samples were ammonium exchanged, calcined, and impregnated with a suitable amount of tetraamineplatinum dichloride to yield 1 wt. % Pt concentration on the final catalyst. The impregnated zeolites were then screened to 40–60 mesh. The meshed catalysts were calcined by ramping to 250° C. at 1° C./min and held there for 2 hr. The test was carried out in a high pressure microreactor operating at atmospheric pressure using 500 mg of the meshed samples. The samples were pretreated in a $H_2$ stream for 2 hr at 300° C. The feed consisted of 100:1$H_2$/decane and the test was conducted over the temperature range from 130° C. to 260° C. at a 10° C./min ramp rate. Products were analyzed via online GC. The data is summarized in the Table 17 below.

TABLE 17

Comparison of MCM-22, MCM-56, and UZM-8 in Decane Conversion Tests

| | Constant Temperature T = 250° C | | | Constant $C_{10}$ Conversion (49%) | | | Constant $C_{10}$ Conversion (44%) | |
|---|---|---|---|---|---|---|---|---|
| Sample | Ex. 5 | MCM-56 | MCM-22 | Ex. 5 | MCM-56 | Ex. 5 | MCM-22 | |
| Temp | 250° C. | 250° C. | 250° C. | 218° C. | 216° C. | 215° C. | 208° C. | |
| $C_{10}$ Conv. | 97.7% | 98.9% | 99.8% | 49% | 49% | 44% | 44% | |
| MeC₉ Isomers | 19.0% | 11.7% | 2.3% | 29.5% | 28.4% | 27.1% | 20.7% | |
| EtC₈ Isomers | 4.1% | 3.2% | 1.5% | 2.1% | 1.9% | 1.8% | 1.0% | |
| Mono-branched $C_{10}$ isomers | 23.1% | 15.0% | 3.8% | 31.6% | 30.3% | 28.9% | 21.7% | |
| Di-branched $C_{10}$ isomers | 10.2% | 9.2% | 2.5% | 3.2% | 4.0% | 2.6% | 4.8% | |
| $C_{10}$ isomers | 33.3% | 24.2% | 6.3% | 34.7% | 34.3% | 31.5% | 26.5% | |
| Cracked products | 64.5% | 74.7% | 93.5% | 14.5% | 15.3% | 13% | 17.8% | |

It is easily seen in the table that UZM-8 is not quite as active as MCM-56 or MCM-22, as the decane conversion is lowest for UZM-8 at constant temperature. The order of activity is MCM-22>MCM-56>UZM-8. The temperatures required to achieve matching conversion for UZM-8 and the other materials is always higher for UZM-8, again confirming the lower activity. However, it is also seen that UZM-8 favors isomerization vs. MCM-56 and MCM-22. The constant temperature results at 250° C. for UZM-8 show significantly more isomerization than either MCM-22 or MCM-56, both of which tend to do a lot more cracking. Direct comparisons at constant conversion also shows UZM-8 tends to do more overall isomerization and less cracking than either MCM-56 or MCM-22. Interestingly, while the overall isomerization for UZM-8 is highest among the three materials at constant conversion, UZM-8 formed more mono-branched decane isomers than either MCM-22 or MCM-56, while at the same time MCM-56 and MCM-22 formed more di-branched decane isomers than UZM-8. Hence, UZM-8 has different catalytic properties than both MCM-22 and MCM-56.

Example 18

An aluminosilicate reaction mixture was prepared by adding 80.44 g of Al(Osec-Bu)₃ (95+%) to 732.97 g of DEDMAOH (20%) with vigorous stirring. This was followed by the addition of 252.7 g of Ultrasil VN SP (85%) silica. Then a solution containing 12.67 g NaOH dissolved in 321.22 g distilled water was prepared and added slowly to the aluminosilicate reaction mixture with continued vigorous stirring. The mixture was homogenized for 30 minutes with a high-speed stirrer. After a half-hour of homogenizing the reaction mixture, 16 g of UZM-8 seeds were added. The reaction mixture was placed in a 2 L stirred autoclave at 150° C. for 185 hours. The solid product was isolated by filtration, washed with de-ionized water, and dried at room temperature.

X-ray powder diffraction analysis showed the product to have the UZM-8 structure. Characteristic diffraction lines for the product are shown in Table 18 below. The UZM-8 sample was ammonium ion-exchanged with a solution that contained 1 g NH$_4$NO$_3$ dissolved in 10 g de-ionized water for every gram of UZM-8. The exchanges was carried out twice, heating for 2 hr at 80° C. each time, with thorough washes in between. A portion of the exchanged product was calcined under a flow of nitrogen for 6 hr at 540° C. The composition of the calcined product exhibited the elemental mole ratio Si/Al=9.47 as determined by elemental analysis. The BET surface area of the calcined material was 427 m$^2$/g and the micropore volume was 0.11 cc/g.

TABLE 18

| 2-θ | d(Å) | I/I$_0$% |
|---|---|---|
| 2.88 | 30.61 | m |
| 6.56 | 13.46 | m |
| 7.12 | 12.40 | s |
| 8.52 | 10.37 | vs |
| 12.78 | 6.92 | w |
| 13.36 | 6.62 | w |
| 14.39 | 6.15 | w |
| 19.80 | 4.48 | m |
| 22.16 | 4.01 | s |
| 24.90 | 3.57 | m |
| 25.90 | 3.44 | vs |
| 26.36 | 3.38 | m |
| 33.25 | 2.69 | w |
| 37.64 | 2.39 | w |
| 45.87 | 1.98 | w |
| 48.60 | 1.87 | w |
| 51.53 | 1.77 | w |
| 65.24 | 1.43 | w |

Example 19

A 23 g portion of the UZM-8 ammonium exchanged composition from example 18 was acid treated as follows. An acidic solution was prepared by diluting 50 g HNO$_3$ (69%) in 88 g de-ionized water. The solution was heated to 98° C. before the addition of the ammonium exchanged UZM-8. The resulting slurry was stirred for 4 hr at 98° C. The product was isolated by filtration, washed with de-ionized water, and dried at 98° C.

The modified product was determined to be UZM-8HS via x-ray powder diffraction analysis. Characteristic diffraction lines for the product are listed in Table 19. Elemental analyses showed the product to have a Si/Al ratio of 22.2. The sample was calcined at 540° C. under nitrogen for 6 hrs. The BET surface area of acid extracted UZM-8 was 515 m$^2$/g with a micropore volume of 0.14 cc/g.

TABLE 19

| 2-θ | d(Å) | I/I$_o$ % |
|---|---|---|
| 4.71 | 18.76 | w |
| 7.21 | 12.25 | s |
| 8.58 | 10.30 | vs |
| 14.50 | 6.10 | m |
| 19.88 | 4.46 | m |
| 22.50 | 3.95 | vs |
| 25.15 | 3.54 | m |
| 26.10 | 3.41 | s |
| 26.82 | 3.32 | m |
| 33.54 | 2.67 | w |
| 46.32 | 1.96 | w |
| 48.94 | 1.86 | w |
| 52.12 | 1.75 | w |
| 65.73 | 1.42 | w |

Example 20

A 115 g portion of the UZM-8 ammonium exchanged from Example 18 was treated by acid extraction. A solution was prepared by diluting 200 g HNO$_3$ (69%) in 500 g de-ionized water. The solution was heated to 98° C. before the addition of the ammonium exchanged UZM-8. The resulting slurry was stirred for 18 hr at 98° C. The product was isolated by filtration, washed with de-ionized water, and dried at room temperature.

The product was identified as UZM-8HS via x-ray powder diffraction analysis. Characteristic diffraction lines for the product are listed in Table 20. Elemental analyses showed the product to have a Si/Al ratio of 20.96. A portion of this sample (26 g) was calcined by ramping at 1° C./min to 560° C. under a N$_2$ atmosphere and held there for 10 hr. The BET surface area of this acid extracted UZM-8HS was 504 m$^2$/g with a micropore volume of 0.14 cc/g.

TABLE 20

| 2-θ | d(Å) | I/I$_o$ % |
|---|---|---|
| 5.14 | 17.19 | w |
| 7.10 | 12.44 | s |
| 8.40 | 10.52 | s |
| 14.34 | 6.17 | m |
| 19.62 | 4.52 | m |
| 22.45 | 3.96 | vs |
| 24.98 | 3.56 | w |
| 25.96 | 3.43 | s |
| 33.17 | 2.70 | w |
| 46.22 | 1.96 | w |
| 52.10 | 1.75 | w |
| 65.25 | 1.43 | w |

Example 21

A 14 g sample of the acid extracted and calcined UZM-8HS sample (Si/Al=20.96) from Example 20 was acid extracted a second time. An acidic solution was prepared by diluting 70 g HNO$_3$ (69%) in 150 g de-ionized water. The solution was heated to 98° C. before adding the acid extracted UZM-8HS. The slurry was stirred for 7 hr at 98° C. The product was isolated by filtration, washed with de-ionized water, and dried at room temperature.

The product had the UZM-8HS structure as indicated by x-ray powder diffraction analysis. Characteristic lines in the diffraction pattern are given in Table 21. Elemental analyses showed the Si/Al ratio to be 40.58, while N$_2$ adsorption measurements gave a BET surface area of 495 m$^2$/g with a micropore volume of 0.13 cc/g.

TABLE 21

| 2-θ | d(Å) | I/I$_o$ % |
|---|---|---|
| 4.40 | 20.05 | m |
| 6.59 | 13.40 | w |
| 7.12 | 12.41 | m |
| 8.46 | 10.45 | s |
| 12.70 | 6.96 | w |
| 14.42 | 6.14 | vs |
| 19.72 | 4.50 | w |
| 22.46 | 3.96 | vs |
| 25.15 | 3.54 | w |
| 26.04 | 3.42 | s |
| 26.92 | 3.31 | m |
| 33.36 | 2.68 | w |
| 37.96 | 2.37 | w |

TABLE 21-continued

| 2-θ | d(Å) | I/I₀ % |
|---|---|---|
| 46.63 | 1.95 | w |
| 65.60 | 1.42 | w |

Example 22

A 7 g portion of the double acid extracted UZM-8HS from Example 22 was further treated with acid. An acidic solution was prepared by diluting 16 g HNO$_3$ (69%) in 161 g de-ionized water. The solution was heated to 98° C. before adding the double acid extracted UZM-8 from Example 4. The slurry was stirred for 19 hr at 98° C. The product was isolated by filtration, washed with de-ionized water, and dried at room temperature.

The product was identified as UZM-8HS via powder x-ray diffraction analysis. Characteristic diffraction lines for the product are given in Table 22. Elemental analyses showed the Si/Al ratio to be 44.51, while N$_2$ adsorption measurements gave a BET surface area of 517 m$^2$/g and a micropore volume of 0.13 cc/g.

TABLE 22

| 2-θ | d(Å) | I/I₀ % |
|---|---|---|
| 4.52 | 19.56 | vs |
| 7.14 | 12.36 | m |
| 8.46 | 10.44 | m |
| 12.74 | 6.94 | w |
| 14.50 | 6.10 | vs |
| 19.86 | 4.47 | w |
| 22.50 | 3.95 | vs |
| 25.13 | 3.54 | w |
| 26.08 | 3.41 | s |
| 29.30 | 3.05 | w |
| 32.97 | 2.71 | w |
| 52.24 | 1.75 | w |
| 65.69 | 1.42 | w |

Example 23

A 28 g portion of a UZM-8 sample (Si/Al=9.47) was calcined by ramping at 3° C./min to 560° C. under an N$_2$ atmosphere and held there for 6 hr before changing the atmosphere to air, and continuing the calcination for another 6 hr. A solution was prepared by diluting 50 g HNO$_3$ (69%) in 88 g de-ionized water. The solution was heated to 98° C. before adding the calcined UZM-8. The slurry was stirred for 4 hr at 98° C. The product was isolated by filtration, washed with de-ionized water, and dried at 75° C. for 12 hr.

The product was identified as UZM-8HS via x-ray powder diffraction analysis. Characteristic diffraction lines for the product are listed in Table 23. Elemental analyses showed the Si/Al ratio to be 24.82, while N$_2$ adsorption measurements gave a BET surface area of 449 m$^2$/g with a micropore volume of 0.12 cc/g.

TABLE 23

| 2-θ | d(Å) | I/I₀ % |
|---|---|---|
| 4.30 | 20.56 | vs |
| 7.14 | 12.37 | m |
| 8.38 | 10.55 | m |
| 12.64 | 7.00 | w |

TABLE 23-continued

| 2-θ | d(Å) | I/I₀ % |
|---|---|---|
| 14.44 | 6.13 | m |
| 19.92 | 4.45 | w |
| 22.62 | 3.93 | s |
| 25.20 | 3.53 | w |
| 26.07 | 3.42 | m |
| 33.30 | 2.69 | w |

Example 24

An aluminosilicate reaction mixture was prepared by adding 80.44 g of Al (Osec-Bu)$_3$ (95+%) to 732.97 g of DEDMAOH (20%) with vigorous stirring. This was followed by the addition of 252.7 g of Ultrasil™ VN SP (85%) silica. A solution containing 12.67 g NaOH dissolved in 321.22 g distilled water was prepared and added slowly to the aluminosilicate mixture with mixing. The resultant mixture was homogenized for 30 minutes with a high-speed stirrer. The reaction mixture was placed in a 2 L stirred autoclave at 150° C. for 285 hours at autogenous pressure. The solid product was isolated by filtration, washed with distilled water, and dried at room temperature.

Analysis by powder x-ray diffraction showed the product to have the UZM-8 structure. Characteristic diffraction lines for the product are listed in Table 24. The UZM-8 sample was ammonium ion-exchanged using a solution that contained 1 g NH$_4$NO$_3$ dissolved in 10 g de-ionized water for every gram of UZM-8. The exchange was carried out twice at 80° C. for two hr, with thorough washing following each exchange. A portion of the product was calcined under a flow of nitrogen for 6 hr at 540° C. The composition of the calcined product exhibited the following mole ratios as determined by elemental analysis: Si/Al=10.51, and Na/Al=0.015. The BET surface area of the calcined material was 432 m$^2$/g and the micropore volume was 0.14 cc/g.

TABLE 24

| 2-θ | d(Å) | I/I₀ % |
|---|---|---|
| 3.02 | 29.23 | m |
| 6.52 | 13.54 | m |
| 7.08 | 12.47 | s |
| 8.56 | 10.32 | vs |
| 13.11 | 6.75 | w |
| 14.31 | 6.19 | w |
| 19.94 | 4.45 | s |
| 22.34 | 3.98 | vs |
| 24.94 | 3.57 | m |
| 25.92 | 3.43 | vs |
| 26.44 | 3.37 | m |
| 31.44 | 2.84 | w |
| 33.32 | 2.69 | w |
| 36.28 | 2.47 | w |
| 37.64 | 2.39 | w |
| 45.99 | 1.97 | w |
| 48.16 | 1.89 | w |
| 52.06 | 1.76 | w |
| 65.27 | 1.43 | w |

Example 25

A 113 g portion of the ammonium exchanged UZM-8 from Example 24 was acid extracted with a solution prepared by diluting 400 g HNO$_3$ (69%) in 67 g de-ionized water. The solution was heated to 98° C. before the addition of the ammonium exchanged UZM-8. The resulting slurry was stirred for 11 hr at 98° C. The product was isolated by filtration, washed with de-ionized water, and dried at 98° C.

The product was identified as UZM-8HS via powder x-ray diffraction analysis. Characteristic diffraction lines for the product are listed in Table 25. Elemental analyses showed the product to have a Si/Al ratio of 49.43. The product was calcined at 540° C. under nitrogen for 6 hrs. The BET surface area of this acid extracted UZM-8HS was 449 m²/g with a micropore volume of 0.14 cc/g.

TABLE 25

| 2-θ | d(Å) | I/I₀ % |
| --- | --- | --- |
| 4.46 | 19.79 | w |
| 7.24 | 12.20 | vs |
| 8.51 | 10.38 | vs |
| 12.86 | 6.88 | w |
| 14.50 | 6.10 | vs |
| 19.80 | 4.48 | s |
| 22.66 | 3.92 | vs |
| 25.12 | 3.54 | w |
| 26.18 | 3.40 | vs |
| 26.86 | 3.32 | m |
| 29.29 | 3.05 | w |
| 33.65 | 2.66 | w |
| 37.90 | 2.37 | w |
| 46.61 | 1.95 | w |
| 52.08 | 1.75 | w |
| 65.74 | 1.42 | w |

Example 26

A 70 g portion of the UZM-8 ammonium exchanged from Example 24 was acid extracted with a solution prepared by diluting 435 g HNO₃ (69%) in 14 g de-ionized water. The solution was heated to 98° C. before the addition of the ammonium exchanged UZM-8. The resulting slurry was stirred for 8.5 hr at 98° C. The product was isolated by filtration, washed with de-ionized water, and dried at 98° C.

The product was identified as UZM-8HS via powder x-ray diffraction analysis. Characteristic diffraction lines for the product are listed in Table 26. Elemental analyses showed the product to have a Si/Al ratio of 80.47. This sample was calcined at 540° C. under a nitrogen atmosphere for 4 hrs. The BET surface area of acid extracted UZM-8HS was 452 m²/g with a micropore volume of 0.15 cc/g.

TABLE 26

| 2-θ | d(Å) | I/I₀ % |
| --- | --- | --- |
| 4.64 | 19.03 | m |
| 6.60 | 13.39 | m |
| 7.18 | 12.30 | vs |
| 8.47 | 10.43 | vs |
| 12.86 | 6.88 | w |
| 14.46 | 6.12 | s |
| 16.15 | 5.48 | w |
| 19.89 | 4.46 | w |
| 22.67 | 3.92 | vs |
| 25.18 | 3.53 | w |
| 26.24 | 3.39 | vs |
| 26.88 | 3.31 | m |
| 33.33 | 2.69 | w |
| 38.03 | 2.36 | w |
| 46.36 | 1.96 | w |
| 49.23 | 1.85 | w |

Example 27

A 70 g portion of the UZM-8 ammonium exchanged from Example 24 was acid treated with a solution prepared by diluting 535 g HNO₃ (69%) in 14 g de-ionized water. The solution was heated to 98° C. before the addition of the ammonium exchanged UZM-8. The resulting slurry was stirred for 15 hr at 98° C. The products were isolated by filtration, washed with de-ionized water, and dried at 98° C.

The product was identified as UZM-8HS by powder x-ray diffraction analysis. Characteristic diffraction lines for the product are listed in Table 27. Elemental analyses showed the product to have a Si/Al ratio of 122. This sample was calcined at 540° C. under nitrogen for 4 hrs. The BET surface area of this acid extracted UZM-8HS was 466 m²/g with a micropore volume of 0.15 cc/g.

TABLE 27

| 2-θ | d(Å) | I/I₀ % |
| --- | --- | --- |
| 4.34 | 20.34 | w |
| 6.53 | 13.53 | w |
| 7.20 | 12.27 | vs |
| 8.64 | 10.22 | m |
| 12.80 | 6.91 | w |
| 14.48 | 6.11 | w |
| 16.10 | 5.50 | w |
| 19.84 | 4.47 | w |
| 22.64 | 3.92 | vs |
| 25.19 | 3.53 | w |
| 26.20 | 3.40 | vs |
| 26.86 | 3.32 | m |
| 31.96 | 2.80 | w |
| 33.72 | 2.66 | w |

Example 28

A UZM-8 sample was prepared by first adding 732.97 g DEDMAOH (20%) to a large beaker followed by the addition of 80.44 g Al sec-butoxide (97%) with vigorous mixing. Then 248.5 g de-ionized water was added to the mixture which was allowed to stir further. Then 252.70 g Ultrasil VN SP (89% SiO₂) was added which led to the formation of a thick gel, which was vigorously mixed. Separately, 8.50 g NaOH was dissolved in 73 g de-ionized water. The latter solution was added to the gel, again while mixing. Finally 16 g UZM-8 seed was added and the mixture was homogenized for an additional 20 minutes. This reaction mixture was transferred to a Parr 2 L stirred reactor where it was digested at 150° C. for 185 hr. The product was isolated by filtration, washed with de-ionized water and dried in air. The product was identified as UZM-8 by powder x-ray diffraction.

A portion of this sample was ammonium exchanged using 1 g NH₄NO₃ dissolved in 10 g de-ionized water for every gram of UZM-8. The exchanges were carried out twice, heating the mixture to 80° C. for 2 hr with thorough washes after each exchange. Elemental analysis showed this material to have an Si/Al ratio of 10.35.

This ammonium exchanged UZM-8 was treated with ammonium hexafluorosilicate to give a dealuminated UZM-8HS. A 3.16 g sample of ammonium hexafluorosilicate was dissolved in 60.10 g de-ionized water. In a separate beaker, 131.45 g of the ammonium exchanged UZM-8 was suspended in 330.5 g de-ionized water and the slurry was heated to 80° C. The ammonium hexafluorosilicate solution was delivered to the zeolite slurry with a pump at a rate of about 0.52 cc/min. Once the addition was completed, the slurry was held at 80° C. for an additional hour. The product was isolated by filtration and washed with 5 liters of de-ionized water and dried at room temperature.

The product was identified as UZM-8HS via powder x-ray diffraction and elemental analysis. Characteristic diffraction lines for the product are given in Table 28. The Si/Al ratio determined from elemental analysis was 11.89, representing a 12% decrease in aluminum content in the zeolite. The product was calcined and subjected to nitrogen adsorption measurements, which yielded a BET surface area of 514 m²/g and a micropore volume of 0.13 g/cc.

TABLE 28

| 2-θ | d(Å) | I/I$_o$ % |
|---|---|---|
| 6.38 | 13.85 | w |
| 7.08 | 12.48 | s |
| 8.58 | 10.30 | vs |
| 12.68 | 6.98 | w |
| 14.27 | 6.20 | w |
| 15.57 | 5.69 | w |
| 19.76 | 4.49 | m |
| 22.30 | 3.98 | m |
| 24.84 | 3.58 | w |
| 25.90 | 3.44 | s |
| 26.64 | 3.34 | m |
| 31.49 | 2.84 | w |
| 33.02 | 2.71 | w |
| 37.57 | 2.39 | w |

Example 29

For examples 30–55, the catalysts were prepared using UZM-8 and its modified derivatives prepared according to Examples 5, 18 or 24 above. The properties of these materials are presented in Table 29.

TABLE 29

Properties of parent UZM-8 materials and MCM-22.

| Material | Si/Al | Surface Area (m²/g, BET) | Micropore Volume (cc/g) |
|---|---|---|---|
| UZM-8, Ex. 5 | 9.96 | 343 | 0.14 |
| UZM-8, Ex. 18 | 9.47 | 427 | 0.11 |
| UZM-8, Ex. 24 | 10.51 | 432 | 0.14 |
| MCM-22 | 14.2 | — | 0.20 |

MCM-22 was prepared according to the following procedure. A gel having the following composition was prepared: 2.7 Na$_2$O:1.0 Al$_2$O$_3$:30SiO$_2$:1681H$_2$O:10.5HMI where HMI is hexamethyleneimine. The gel was placed in an autoclave and reacted at 160° C. for 7 days with stirring. The solid material was isolated, washed, dried and then calcined in air at 538° C. for 20 hours. Finally the MCM-22 was ammonium exchanged and was found to have a Si/Al of 14 and <0.005 wt. % Na. The sample was then formulated into a catalyst comprising 70 wt % MCM-22 and 30 wt % alumina in 1/16" diameter extrudates. This extrusion was done by using acid peptized Al$_2$O$_3$ to bind the zeolite and Solka Floc™ as an extrusion aid. The extrudate was activated in a flow of air first at 454° C., then 510° C. prior to testing.

Example 30

A portion of the UZM-8 product from Example 5 was ammonium ion exchanged (1225 ml of 1.25M NH$_4$NO$_3$ heated to ~75° C. for 2 h and repeated). The sample was then formulated into a catalyst comprising 70 wt % UZM-8 and 30 wt % alumina. The extrusion was done using HNO$_3$-peptized Al$_2$O$_3$ as a binder and Solka Floc™ as an extrusion aid to obtain 1/16" diameter extrudates. The extrudates were activated in a muffle oven by heating to 538° C. and holding there for one hour in a N$_2$ flow, and then switching to air and holding for 15 hours.

Example 31

The catalytic performance of the MCM-22 derived catalyst of Example 29 and the UZM-8 derived catalyst of Example 30 in ethylbenzene (EB) synthesis via benzene alkylation with ethylene is summarized in Table 31. Both catalysts were evaluated using a testing methodology where the product effluent is recycled to combine with the fresh feeds of benzene and ethylene. The UZM-8 derived catalyst exhibited high activity and higher total alkylated selectivity as shown in Table 31. The comparison of mono-alkylated selectivity is not valid, since MCM-22 activity is much lower and ethylene broke through the bed.

TABLE 31

MCM-22 versus UZM-8 in EB Synthesis
Conditions: 550 psig, product effluent recycle, C$_2^=$ LHSV = 0.45 hr$^{-1}$, Bz/C$_2^=$~3
Catalyst: 70/30 zeolite/Al$_2$O$_3$ in 1/16 inch diameter extrudate

| Example | Example 29 | | | Example 30 | |
|---|---|---|---|---|---|
| Bz/C$_2^=$ | 2.78 | 2.69 | 2.62 | 2.62 | 2.63 |
| Inlet Temp. (° C.) | 212 | 221 | 234 | 220 | 200 |
| Active Zone (fraction of bed) | 0.55 | 0.55 | 0.42 | 0.22 | 0.26 |
| Ethylbenzene | 81.76 | 80.25 | 79.04 | 78.60 | 79.15 |
| EB + DEB + TEB + TeEB* | 98.94 | 98.31 | 97.67 | 99.61 | 99.64 |
| unconverted C$_2^=$ | 0.71 | 1.42 | 2.13 | 0.00 | 0.00 |

*DEB = diethylbenzene; TEB = triethylbenzene; TeEB = tetraethylbenzene

Example 32

A UZM-8 sample was prepared according to Example 5 above, providing a product with a Si/Al ratio of 9.4. The zeolite was ammonium ion-exchanged and formed into a catalyst according to the procedure given in Example 30.

Example 33

UZM-8HS was prepared as per Example 19. It was formulated into a catalyst consisting of 70 wt % zeolite and 30 wt % $Al_2O_3$. The extrusion was done using $HNO_3$-peptized $Al_2O_3$ as a binder and Solka Floc™ as an extrusion aid to obtain 1/16" diameter extrudates. The extrudates were activated in a muffle oven by first heating to 538° C. and holding there for one hour in a $N_2$ flow, and then switching to air and holding for 15 hours.

Example 34

The catalysts of Examples 32 and 33 were tested for ethylbenzene (EB) synthesis via the alkylation of benzene with ethylene. In contrast to Example 31, the catalysts were tested in the once through mode without product effluent recycle. Variables in the tests included inlet temperature and benzene to ethylene ratio. The performance of the UZM-8 catalysts is summarized in Table 32. The data clearly show that the UZM-8 and -8HS derived catalysts give good mono-alkylated and total alkylated product selectivity. After testing the UZM-8HS catalyst was regenerated at 540° C. in an air flow to remove the carbonaceous material deposited thereon. As shown in Table 32, the performance of the regenerated catalyst was found to be comparable to the fresh catalyst.

TABLE 32

Ethylbenzene Synthesis with UZM-8/$Al_2O_3$ Catalyst Conditions: 550 psig; 0.45 hr⁻¹ LSHV; Once through mode

| Example | Benzene/Ethylene | Inlet Temp. (° C.) | EB Selectivity | EB + DEB + TEB + TeEB* (Total Alkylate) |
|---|---|---|---|---|
| 32 | 9.6 | 220 | 92.9 | 99.9 |
| 32 | 9.4 | 200 | 93.5 | 99.9 |
| 32 | 6.6 | 180 | 91.2 | 99.9 |
| 33 | 8.9 | 220 | 93.5 | 99.9 |
| 33 | 8.9 | 200 | 94.1 | 99.9 |
| 33 | 6.3 | 180 | 92.7 | 99.9 |
| 33 regenerated | 8.7 | 220 | 92.8 | 99.8 |
| 33 regenerated | 8.4 | 200 | 93.6 | 99.9 |
| 33 regenerated | 6.1 | 180 | 91.7 | 99.9 |

*DEB = Diethylbenzene; TEB = Triethylbenzene; TeEB = Tetraethylbenzene

Example 35

The UZM-8/$Al_2O_3$ catalyst prepared in Example 32 was also tested for aromatic transalkylation activity. The test was conducted at 400 psig pressure with 4:1 hydrogen:hydrocarbon ratio using a feed that contained 15% toluene, 60% A9 (propylbenzene, methylethylbenzene and trimethylbenzene) and 25% A10 (tetramethylbenzene and a small amount of butylbenzene). The catalytic performance in this test is summarized in Table 33, for a target of 36% conversion. As shown in Table 33, the UZM-8-containing catalyst was shown to be significantly more active than a reference mordenite catalyst with only slightly lower selectivity to xylenes.

TABLE 33

UZM-8 vs. Mordenite reference in catalyzed aromatic transalkylation

| Catalyst | Temp. (° C.) | Benzene | EB | Xylenes | Heavies | Lights | Non-Aromatic |
|---|---|---|---|---|---|---|---|
| MOR ref | 430 | 4.44 | 4.20 | 26.57 | 13.06 | 49.09 | 0.86 |
| MOR ref | 413 | 4.16 | 4.82 | 26.73 | 14.27 | 46.64 | 1.23 |
| Example 32 | 394 | 5.92 | 3.96 | 24.10 | 12.99 | 49.29 | 0.79 |

Example 36

The UZM-8 zeolite of Example 5 was ammonium exchanged and formed into a catalyst per the procedure of Example 30 except that the catalyst contained 20 wt % UZM-8 and 80 wt % alumina The calcined support was impregnated with a solution of chloroplatinic acid to give 0.3 wt % Pt, followed by air oxidation and $H_2$ reduction. The reduced catalyst was then sulfided at room temperature prior to catalytic evaluation.

Example 37

The catalyst described in Example 36 was tested for xylene and ethylbenzene isomerization. For comparison purposes, a catalyst made with mordenite and $Al_2O_3$ in the shape of 1/16" diameter spheres was prepared using oil dropping technique, impregnated with Pt, calcined, reduced with $H_2$ and then sulfided using a procedure similar to that described in Example 36. The feed composition and test conditions are summarized in Table 34. The activity is defined as the ratio of para-xylene to total xylene (PX/X) ratio, a measurement indicative of degrees of reaction advancing toward equilibrium composition. It is desirable to achieve catalytic performance of high activity (higher PX/X) and lower $C_8$ ring loss. The WHSV was adjusted to vary activity. The results for UZM-8 and mordenite are summarized in FIGS. 1 and 2.

TABLE 34

Process Conditions/Feed for Example 36

| | |
|---|---|
| pressure, psig | 100 |
| $H_2$/feed | 4 |
| temperature, (° C.) | 365–385 |
| WHSV, hr⁻¹ | 3.5 |
| Feed, wt % | |
| Non-aromatics | 11.11 |
| Benzene | 0.02 |
| Toluene | 0.80 |
| Ethylbenzene | 16.25 |
| p-Xylene | 0.23 |
| m-Xylene | 48.51 |
| o-Xylene | 23.02 |
| $C_{9+}$ | 0.07 |

In the following examples describing the modified materials, Table 35 serves as a key to the parent materials and the modifications carried out. In some cases, the preparation of the parent material was altered by the addition of UZM-8 seed crystals. The details of the preparation of these materials are elaborated on below. Also tabulated are the Si/Al ratios of the modified materials.

TABLE 35

Modified UZM-8 Materials: Parent UZM-8, Modification Scheme, Si/Al ratio

| Example | Parent Material | Modification Steps in order | Si/Al |
|---|---|---|---|
| 38 | Example 24 w/seed | $NH_4^+$ - Cal - AW -Cal | 24.3 |
| 39 | Example 18 | $NH_4^+$ - AW - Cal | 29.28 |
| 40 | Example 24, w/seed | $NH_4^+$ - AW - Cal | 22.44 |
| 41 | Example 24, w/seed | $NH_4^+$ - Cal | 10.35 |
| 42 | Example 18 | $NH_4^+$ - Cal | 10.11 |
| 43 | Example 24, w/seed | $NH_4^+$ - AFS - Cal | 11.89 |
| 45 | Example 18 | $NH_4^+$ - Cal | 10.11 |
| 46 | Example 18 | $NH_4^+$ - AW - Cal | 19.74 |
| 47 | Example 24 | AW - Cal | ND |
| 49 | Example 18 | $NH_4^+$ - Cal | 9.82 |
| 50 | Example 18 | $NH4^+$ - Cal-AW - Cal | 13.15 |
| 51 | Example 24 | $NH_4^+$ - Cal-AW - Cal | 18.46 |
| 52 | Example 24 | $NH_4^+$ - Cal | 11.06 |
| 53 | Example 24 | $NH_4^+$ - AFS - Cal | 17.53 |
| 55 | Example 24 | $NH_4^+$ - AFS - Cal | 18.54 |

Key:
$NH_4^+$ = Ammonium ion exchange;
Cal = calcination;
AW = acid wash;
AFS = ammonium hexafluorosilicate treatment;
ND = not determined Example 38

An ammonium exchanged UZM-8, prepared per Example 40 below, was calcined at 540° C. for 16 hr in air. A 12 g portion of the resulting product was suspended in a nitric acid solution (50 g $HNO_3$ (69%) diluted in 88 g deionized water) that had previously been heated to 98° C. The UZM-8 was slurried in this solution for 4 hr at 98° C., isolated by filtration, washed with deionized water and dried at 70° C. The material was then calcined at 540° C., initially in nitrogen and finally under a flow of dry air for a total of 6 hr.

Example 39

A UZM-8 sample from Example 18 was ammonium exchanged according to the procedure in Example 40 below. A 14 g portion of the exchanged zeolite was suspended in a nitric acid solution (35 g $HNO_3$ (69%) diluted in 120 g deionized water) that had previously been heated to 98° C. and the resulting slurry was heated for 4 hr. The product was isolated by filtration, washed with deionized water, and dried at 98° C. The product was then calcined at 540° C., initially in nitrogen and finally under a flow of dry air for a total of 6 hr.

Example 40

This material is identical to that in Example 19 above.

Example 41

A zeolite sample from Example 24 was ammonium exchanged using a preferred ion exchange procedure that has been applied to many of the modified materials in this application. An ammonium nitrate solution was prepared that contained 1 g $NH_4NO_3$ dissolved in 10 g deionized water, for each gram of zeolite to be exchanged. A slurry of the zeolite and the ammonium nitrate solution was then heated to 70° C. and held there for 2 hours. The solid was isolated and the exchange was repeated again. After the second exchange, the solid was washed with deionized water and dried. The modified zeolite was then calcined at 540° C. for 16 hr under a flow of dry air.

Example 42

A zeolite sample from Example 18 was ammonium exchanged according to the procedure in Example 41. A portion of the zeolite product was heated at 540° C. for 16 hr under a flow of dry air.

Example 43

A zeolite sample from Example 24 was ammonium exchanged according to the procedure given in Example 41. The material was then treated with ammonium hexafluorosilicate (AFS). A 3.16 g portion of $(NH_4)_2SiF_6$ was dissolved in 60.10 g deionized water. Separately, 131.45 g of the ammonium exchanged UZM-8 zeolite was slurried in 330 g deionized water and heated to 80° C. The AFS solution was then pumped into the zeolite slurry at a rate of 0.52 cc/min while maintaining the temperature at 80° C. When the addition concluded, the slurry was held at 80° C. for an additional hour. The solid was isolated by filtration, washed with 5 l deionized water and dried at room temperature. The product was calcined at 540° C. for 16 hr under a flow of dry air.

Example 44

Figure 3:
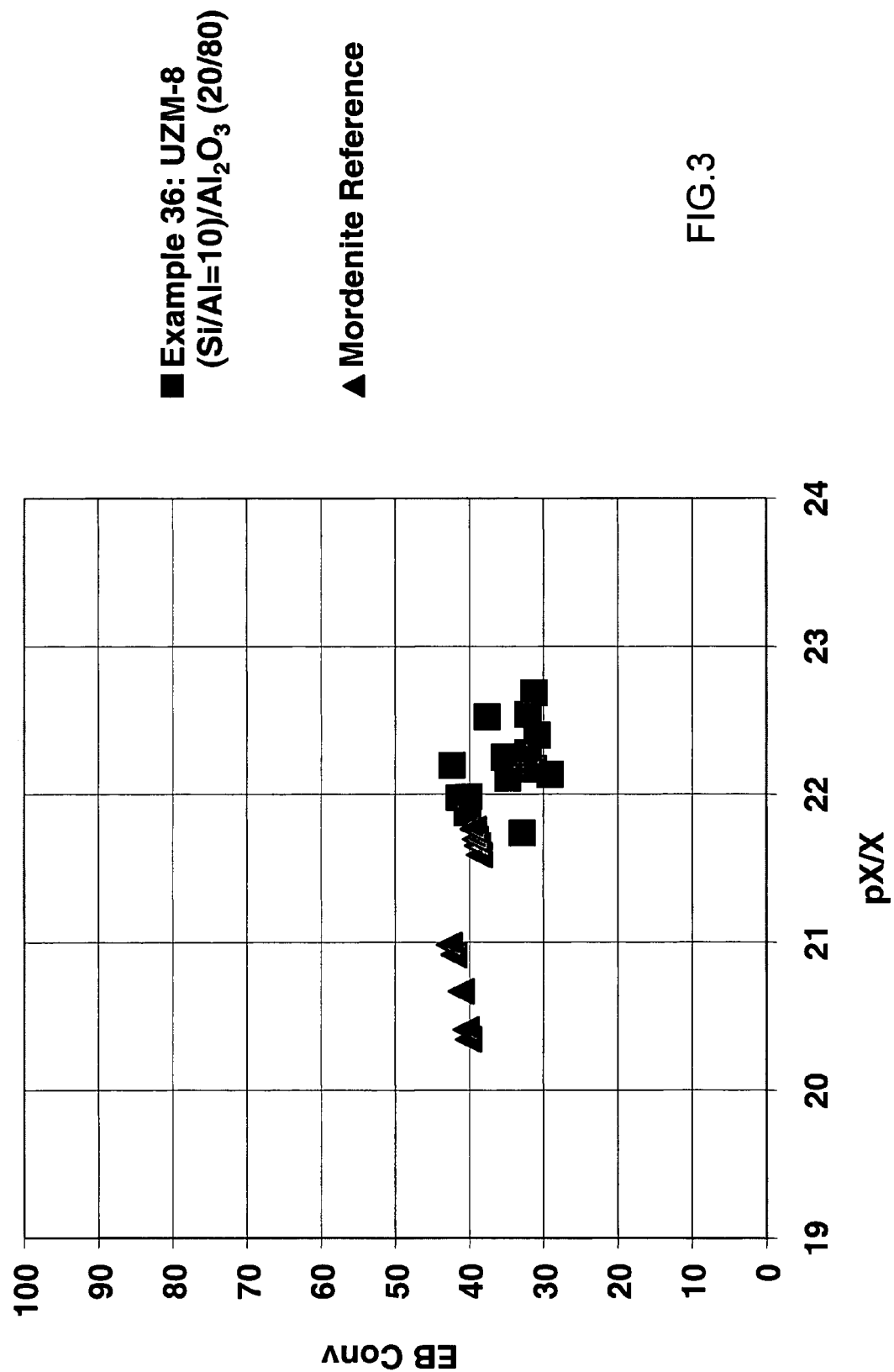
FIG. 3 presents plots of PX/X versus EB conversion for UZM-8 from example 36 and a mordenite reference.

The zeolites described in Examples 38 through 43 in the form of 20–50 mesh particles were tested for xylene isomerization per the procedure described in Table 34 and Example 37. As shown in FIG. 3, the efficiency of xylene isomerization was greatly improved by modifications as well as by the choice of the parent UZM-8.

Example 45

The ammonium exchanged zeolite of Example 42 was mixed with alumina (20 wt % zeolite and 80 wt % alumina), extruded, calcined, loaded with 0.3 wt. % Pt calcined in air, reduced in $H_2$ and sulfided via the procedure in Example 36.

Example 46

A 300 g portion of the ammonium exchanged zeolite from example 42 was slurried in a nitric acid solution (1116 g $HNO_3$ (69%) dissolved in 700 g deionized water) that had been previously heated to 98° C. The slurry was kept at 98° C. for 3 hr, isolated by filtration and washed with deionized water. A portion of this material was mixed with alumina (20 wt % zeolite and 80 wt. % alumina), extruded, calcined, loaded with 0.3 wt % Pt calcined in air, reduced in $H_2$ and sulfided according to the procedure in Example 36.

Example 47

A 36 g portion of the zeolite from Example 24 was suspended in a nitric acid solution (100 g $HNO_3$ (69%) dissolved in 200 g deionized water) previously heated to 98° C. The slurry was held at 98° C. for 4 hr. The product was isolated by filtration, washed with deionized water, and dried at room temperature. A portion of this material was formed into an extrudate catalyst comprising 20 wt % of the zeolite and 80% alumina which was calcined, loaded with 0.3 wt % Pt calcined in air, reduced in H$_2$ and sulfided according to the procedure given in Example 36.

Example 48

Figure 4:
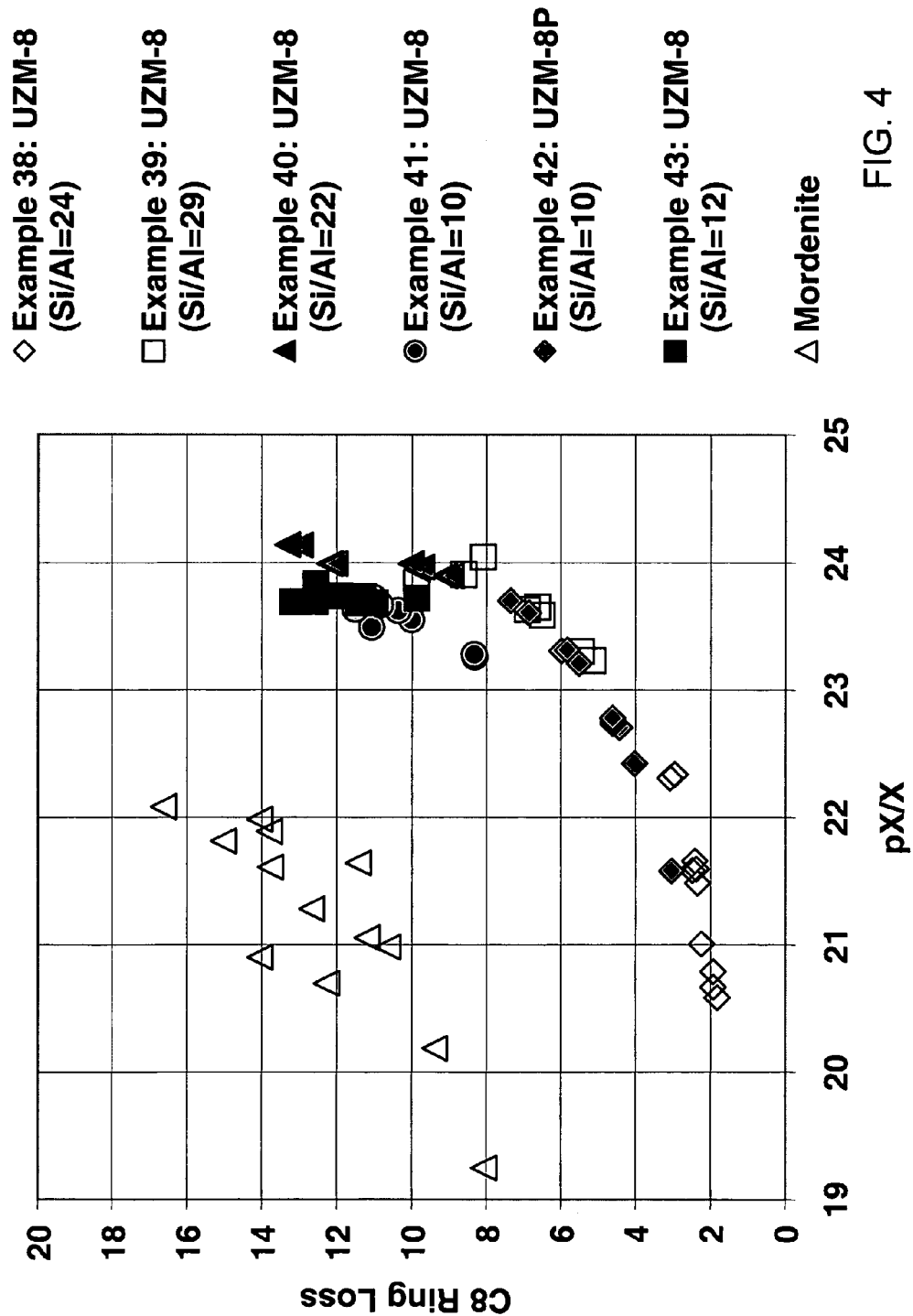
FIG. 4 presents plots of PX/X versus $C_8$ ring loss for catalysts from examples 38–43 and mordenite.
Figure 5:
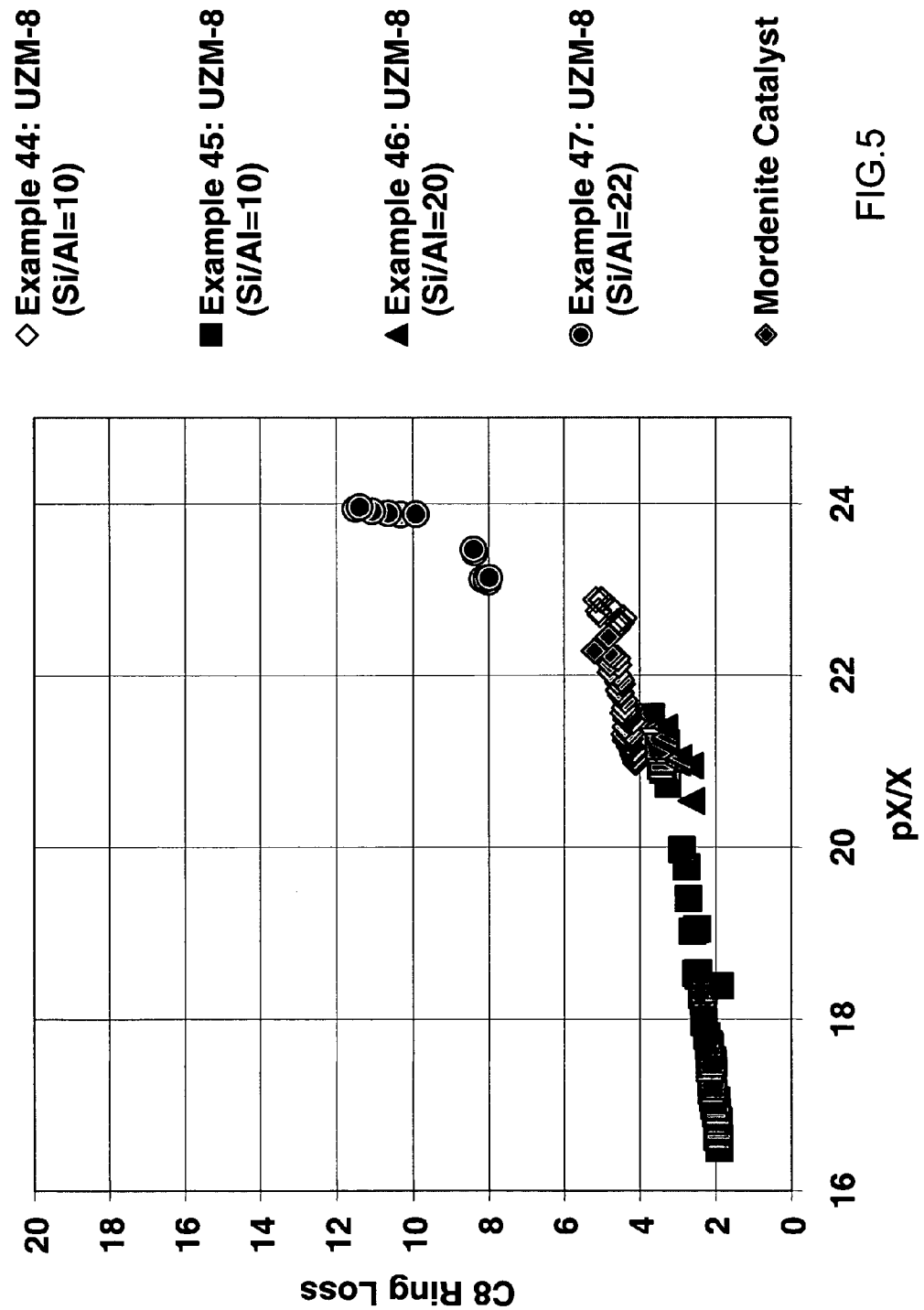
FIG. 5 presents plots of PX/X versus $C_8$ ring loss for catalysts from examples 44 to 47 and mordenite.

The catalysts described in Examples 44 through 47 were evaluated for xylene and ethylbenzene isomerization performance using the test procedure of Example 37. A reference catalyst containing mordenite as per the procedure described in Example 37 was also evaluated. As shown in FIGS. 4 and 5, the performance of the UZM-8 finished catalysts was improved via modification and showed a dependence on the choice of parent UZM-8.

Example 49

A 75 g portion of the zeolite from Example 18 was ammonium exchanged twice using an ammonium nitrate solution (75 g NH$_4$NO$_3$ dissolved in 750 g deionized water) at 80° C. for 2 hr. The product was washed with deionized water and dried in air. The material was then calcined at 540° C. in flowing dry air for 10 hr.

Example 50

A 4.5 g portion of the calcined zeolite from Example 49 was additionally treated with an oxalic acid solution (6.84 g oxalic acid dissolved in 26.65 g deionized water). The oxalic acid solution was heated to 50° C. to achieve full dissolution before the zeolite was added. After the zeolite addition, the temperature of the mixture was increased to 71° C. and held there for 2 hr. The product was isolated by filtration and washed with deionized water. A portion of the dried product was calcined at 375° C. for 3 hr under flowing dry air.

Example 51

A 4.5 g portion of the calcined zeolite from Example 52 was additionally treated with an oxalic acid solution (6.84 g oxalic acid dissolved in 26.65 g deionized water). The oxalic acid solution was heated to 50° C. to achieve full dissolution before the zeolite was added. After the zeolite addition, the temperature of the mixture was increased to 71° C. and held there for 2 hr. The product was isolated by filtration and washed with deionized water. The dried product was calcined at 375° C. for 3 hr under flowing dry air.

Example 52

A 75 g portion of the zeolite from Example 24 was ammonium exchanged twice in an ammonium nitrate solution (75 g NH$_4$NO$_3$ dissolved in 750 g deionized water) at 80° C. for 2 hrs. The product was washed with deionized water and dried in air. A portion of the material was then calcined at 540° C. in flowing dry air for 10 hr.

Example 53

A 37 g portion of the ammonium exchanged zeolite from Example 52 (prior to calcination) was treated with ammonium hexafluorosilicate (AFS). An AFS solution was prepared by dissolving 4.35 g (NH$_4$)$_2$SiF$_6$ in 450 g deionized water. The zeolite was slurried in this solution for 17 hr at 90° C. The product was isolated by filtration, washed with deionized water and dried at 50° C.

Example 54

Figure 6:
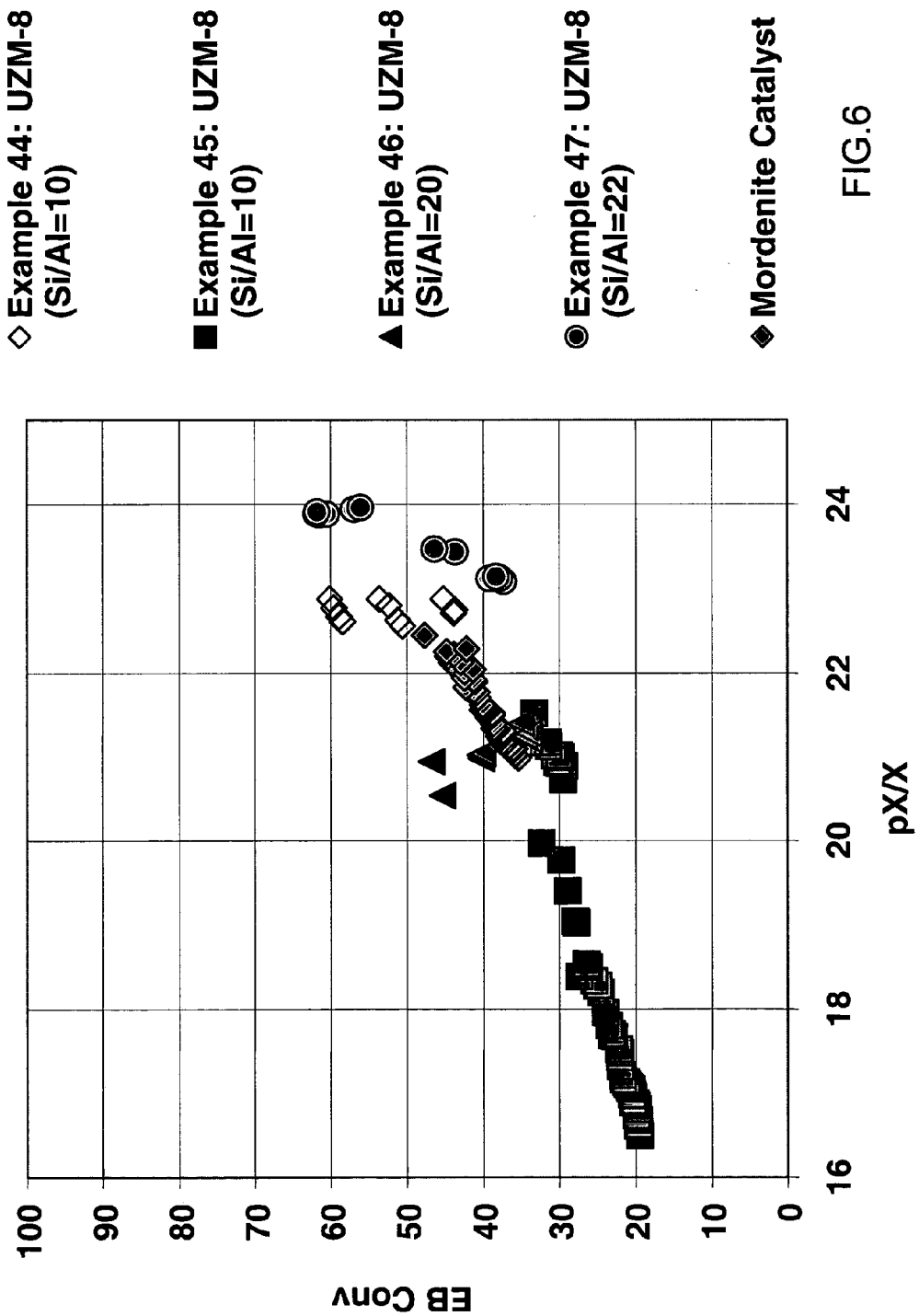
FIG. 6 presents plots of PX/X versus EB conversion for catalysts from examples 44 to 47 and mordenite.

The zeolites from Examples 49 through 53 were formed into 20–50 mesh particulates and tested for xylene isomerization via the procedure of Example 37. As shown in FIG. 6, the efficiency of xylene isomerization was greatly improved by modification and by selection of the parent UZM-8 material.

Example 55

A 120 g portion of ammonium exchanged UZM-8 zeolite from example 24 was treated with ammonium hexafluorosilicate solution (13.9 g (NH$_4$)$_2$SiF$_6$ dissolved in 1440 g deionized water) at 90° C. for 17 hr. The product was isolated by filtration, washed with deionized water and dried. The product was calcined at 540° C. for 16 hr under a flow of dry air. The resulting AFS-UZM-8 was mixed with alumina (10 wt % zeolite and 90 wt % Al$_2$O$_3$), extruded, calcined, loaded with 0.3 wt % Pt calcined in air, reduced in H$_2$ and then sulfided.

Example 56

Figure 7:
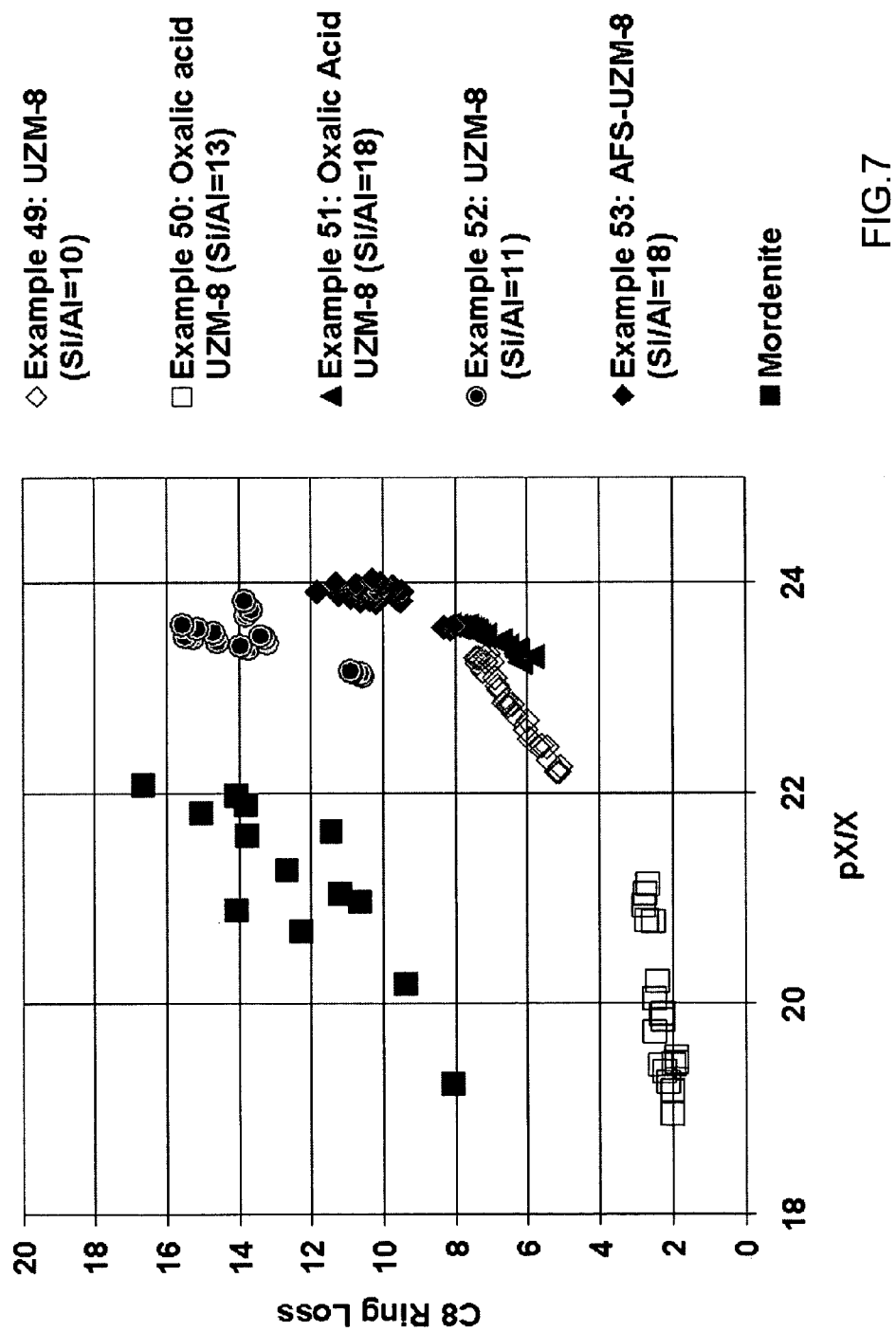
FIG. 7 presents plots of PX/X versus $C_8$ ring loss for catalysts from examples 49 to 53 and mordenite.
Figure 8:
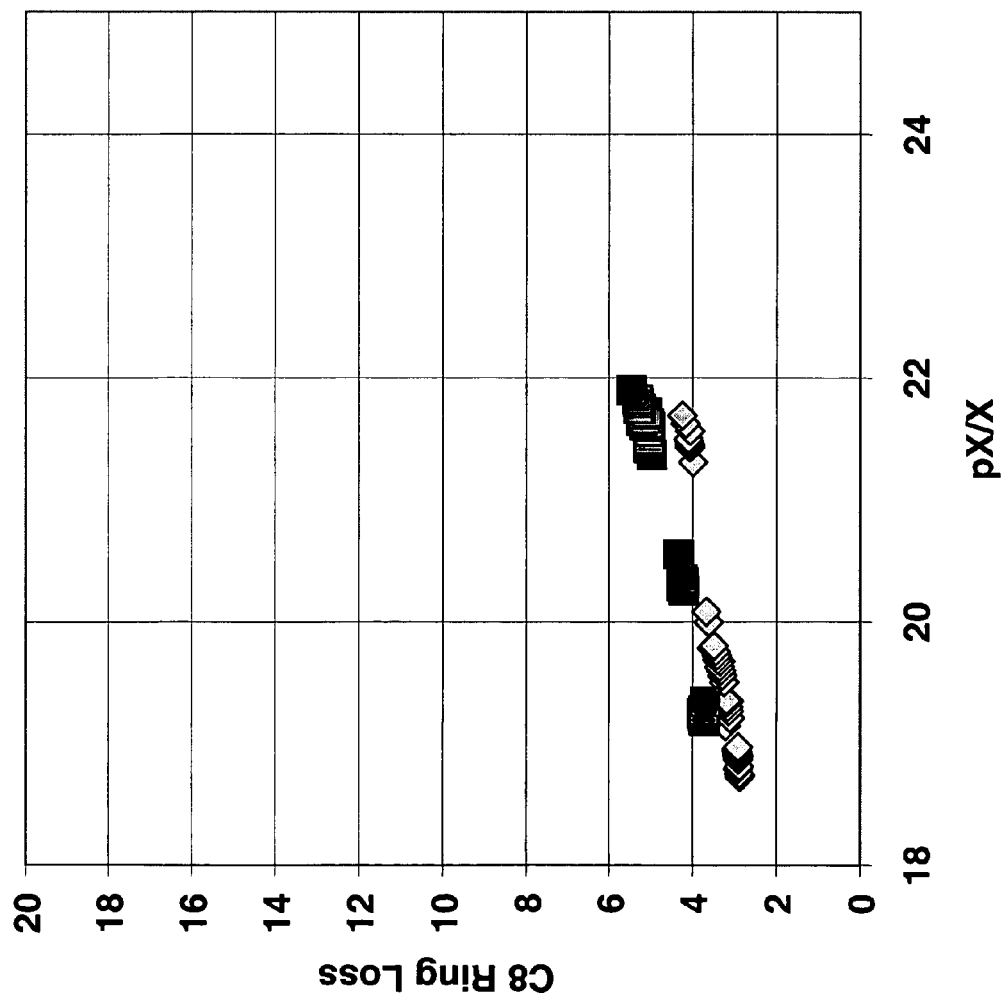
FIG. 8 presents plots of PX/X versus $C_8$ ring loss for the example 55 catalyst and mordenite.

The catalyst described in Example 55 was evaluated for xylene and ethylbenzene isomerization performance as previously described. A catalyst made of mordenite was also evaluated for comparison as per Example 37. As shown in FIGS. 7 and 8, the performance of UZM-8 finish catalyst was improved by modification of UZM-8.

Example 57

Figure 9:
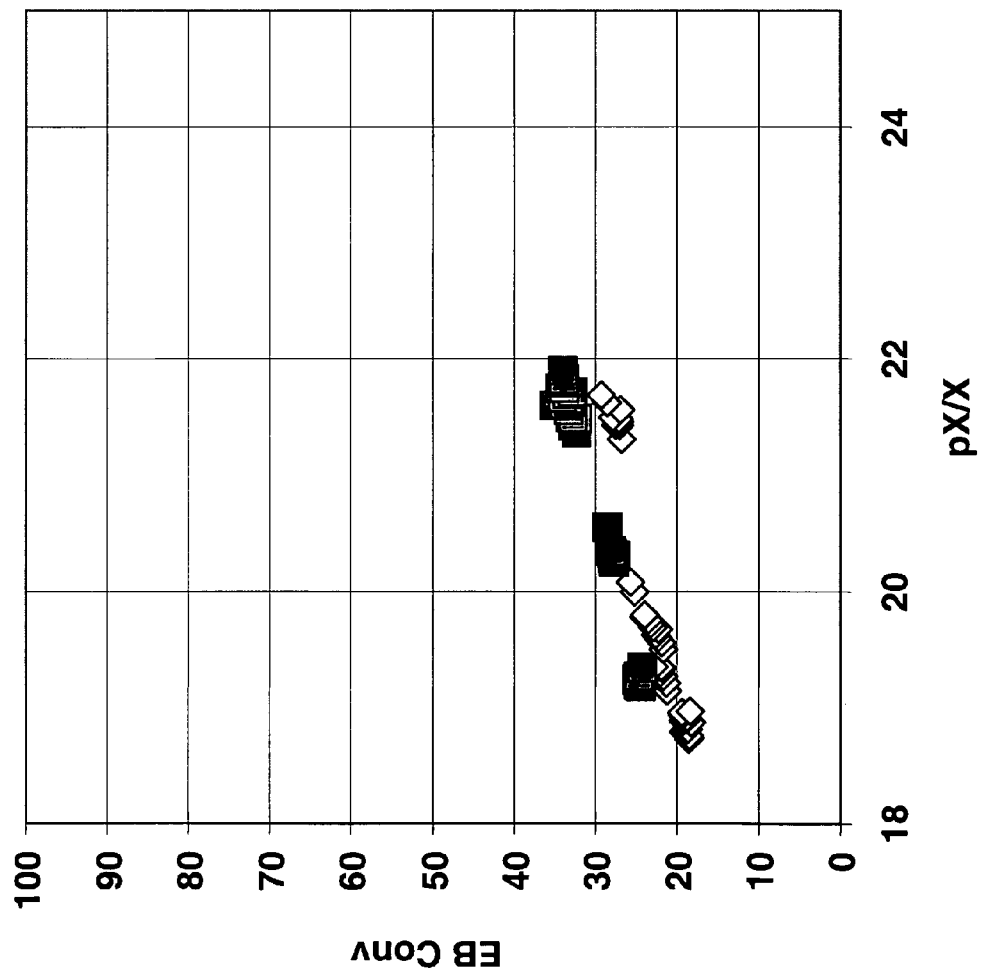
FIG. 9 presents plots of PX/X versus EB conversion for the example 55 catalyst and mordenite.
Figure 10:
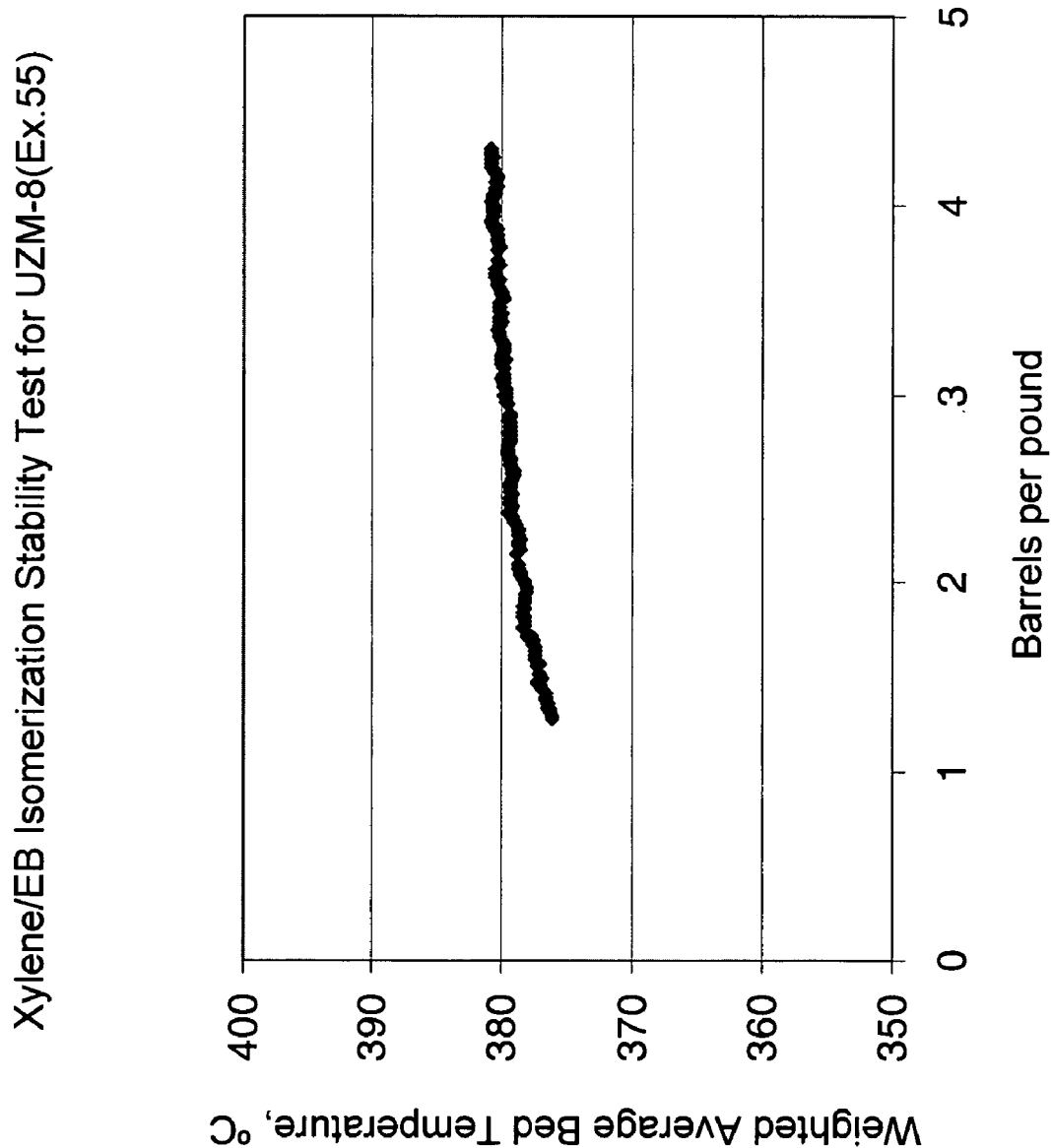
FIG. 10 presents a plot of barrels per pound (catalyst life) versus weighted average bed temperature (° C.) for the catalyst of example 55.
Figure 11:
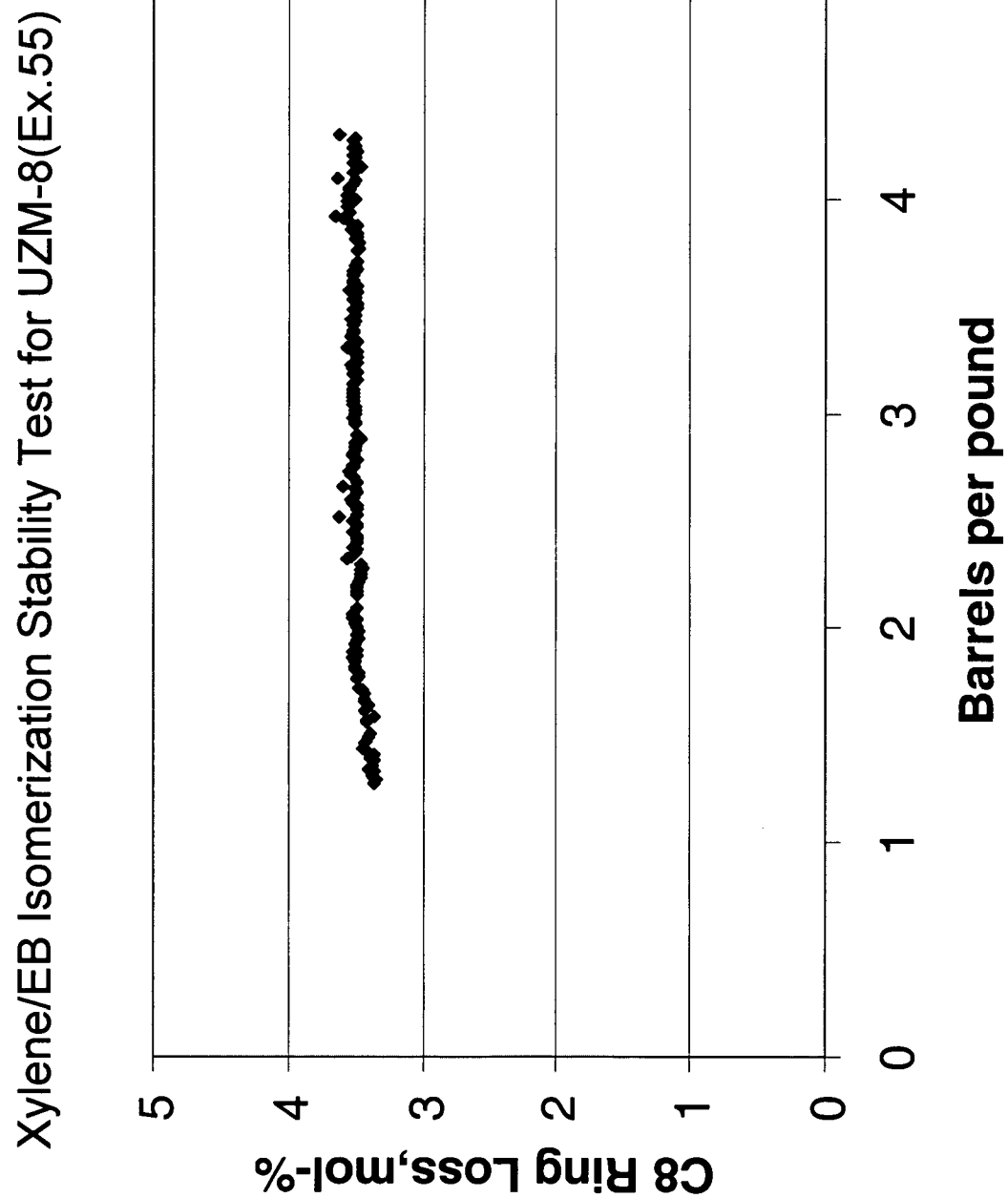
FIG. 11 presents a plot of barrels per pound versus $C_8$ ring loss for the catalyst of example 55.

The catalyst described in Example 55 was evaluated for xylene and ethylbenzene isomerization performance in an accelerated stability test to gauge the long-term stability. The feed was p-xylene depleted and contained 15 wt % EB, 52% m-xylene, 25% o-xylene with balance C$_8$ non-aromatics. The test was conducted at 4 LHSV, 4H$_2$/HC at a constant approach to xylene isomerization equilibrium (pX/X=22.3 and oX/X=24.4). As shown in FIGS. 9 and 10, the catalyst has good stability for xylene isomerization and its C$_8$ ring loss remains constant over the duration of the test.

What is claimed is:

1. A hydrocarbon conversion process comprising contacting a hydrocarbon stream with a catalytic composite at hydrocarbon conversion conditions to give a converted product, the hydrocarbon conversion process selected from the group consisting of alkylation of aromatics, alkylation of isoparaffins, transalkylation of aromatics and isomerization of aromatics and the catalytic composite comprises a UZM-8 zeolite; wherein UZM-8 has a layered framework of at least AlO$_2$ and SiO$_2$ tetrahedral units and a composition on an as-synthesized and anhydrous basis expressed by an empirical formula of:

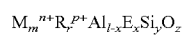

where M is at least one exchangeable cation selected from the group consisting of alkali and alkaline earth metals, "in" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanolamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n+r \cdot p+3+4y)/2$$

and is characterized in that it has the x-ray diffraction pattern having at least the d spacings and intensities set forth in Table A:

TABLE A

| 2-θ | d(Å) | $I/I_0$ % |
|---|---|---|
| 6.40–6.90 | 13.80–12.80 | w–s |
| 6.95–7.42 | 12.70–11.90 | m–s |
| 8.33–9.11 | 10.60–9.70 | w–vs |
| 19.62–20.49 | 4.52–4.33 | m–vs |
| 21.93–22.84 | 4.05–3.89 | m–vs |
| 24.71–25.35 | 3.60–3.51 | w–m |
| 25.73–26.35 | 3.46–3.38 | m–vs. |

2. The process of claim 1 where the hydrocarbon conversion process is alkylation of aromatics.

3. The process of claim 1 where the hydrocarbon conversion process is transalkylation of aromatics.

4. The process of claim 1 where the hydrocarbon conversion process is isomerization of aromatics and the catalytic composite further comprises at least one platinum group metal.

5. The process of claim 1 where the hydrocarbon conversion process is alkylation of isoparaffins.

6. The process of claim 2 wherein the alkylation process comprises monoalkylation of aromatic compounds where an alkylatable aromatic compound is reacted with an olefin under alkylation conditions to provide an alkylated compound.

7. The process of claim 6 where the aromatic compound is benzene, the olefin is propylene and the alkylated compound is cumene.

8. The process of claim 6 where the alkylatable aromatic compound is selected from the group consisting of benzene, naphthalene, anthracene, phenanthrene and substituted derivates thereof.

9. The process of claim 6 where the olefin contains from 2 up to about 20 carbon atoms.

10. The process of claim 3 where the hydrocarbon stream comprises polyisopropyl benzene and benzene.

11. The process of claim 4 where the hydrocarbon stream comprises a non-equilibrium mixture of xylenes and ethylbenzene.

12. The process of claim 4 where the platinum group metal is platinum and is present from about 0.01 to about 5 mass-% of the catalytic composite on an elemental basis.

13. The process of claim 1 where the zeolite is thermally stable up to a temperature of about 600° C.

14. The process of claim 1 where M is selected from the group consisting of lithium, sodium, cesium, strontium, barium and mixtures thereof.

15. The process of claim 1 where R is selected from the group consisting of diethyldimethylammonium, ethyltrimethylammonium, hexamethonium and mixtures thereof.

16. The process of claim 1 where "m" is zero.

17. The process of claim 6 where the aromatic compound is benzene, the olefin is ethylene and the alkylated compound is ethylbenzene.

* * * * *

UNITED STATES PATENT AND TRADEMARK OFFICE
CERTIFICATE OF CORRECTION

PATENT NO. : 7,091,390 B2  Page 1 of 1
APPLICATION NO. : 10/828989
DATED : August 15, 2006
INVENTOR(S) : Deng-Yang Jan et al.

It is certified that error appears in the above-identified patent and that said Letters Patent is hereby corrected as shown below:

<u>Column 46</u>
Claim 1, line 59, replace "in" with --m--.

Signed and Sealed this

Seventh Day of November, 2006

JON W. DUDAS
*Director of the United States Patent and Trademark Office*